US006482803B1

(12) United States Patent
Roth et al.

(10) Patent No.: US 6,482,803 B1
(45) Date of Patent: Nov. 19, 2002

(54) MODIFICATION OF MUTATED P53 GENE IN TUMORS BY RETROVIRAL DELIVERY OF RIBOZYME A

(75) Inventors: Jack A. Roth, Houston, TX (US); De Wei Cai, Cheltenham, PA (US); Tapas Mukhopadhyay, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1220 days.

(21) Appl. No.: 08/523,030

(22) Filed: Sep. 1, 1995

(51) Int. Cl.$^7$ .......................... C07H 21/00; A61K 48/00

(52) U.S. Cl. ...................... 514/44; 435/69.1; 435/91.31; 435/320.1; 435/375; 536/23.2; 536/24.5

(58) Field of Search ............................... 435/69.1, 91.1, 435/91.31, 91.33, 172.1, 172.3, 320.1, 240.1, 240.2, 375, 325, 377; 514/44; 536/23.1, 23.5, 24.5, 23.2

(56) References Cited

U.S. PATENT DOCUMENTS

| 4,554,101 A | 11/1985 | Hopp |
| 5,354,855 A | 10/1994 | Cech et al. |
| 5,399,346 A | 3/1995 | Anderson et al. |
| 5,527,676 A | 6/1996 | Vogelstein et al. |

FOREIGN PATENT DOCUMENTS

| EP | 0 273 085 A1 | 7/1988 |
| WO | WO94/24297 | 10/1994 |
| WO | WO95/02697 | 1/1995 |
| WO | WO 95/11301 | 4/1995 |
| WO | WO 95/13378 | 5/1995 |

OTHER PUBLICATIONS

Report and Recommendations of the Panel to Assess the NIH Investment in Research on Gene Therapy, Orkin and Motulsky, co–chairs. National Institutes of Helath, Dec. 7, 1995.*
Christoffersen et al. Ribozymes as Human Therapeutic Agents. J. Med. Chem. 38(12):2023–2037, Jun. 1995.*
Crystal. Transfer of Genes to Humans: Early Lessons and Obstacles to Success. Science 270: 404–410, Oct. 1995.*
Stull et al. Antigene, Ribozyme, and Aptamer Nucleic Acid Drugs: Progress and Prospects. Pharm. Res. 12(4): 465–481, Apr. 1995.*
Eliyahu et al., "p53—A Potential Suppressor Gene?" *Journal of Cellular Biochemistry*, UCLA Symposia on Molecular & Cellular Biology, Abstracts, 19th Annual Meeting, Supplement 14C:264, Abstract No. I 030, Feb. 3–Mar. 11, 1990.
Hinds, "Biological Consequences of Mutation of the p53 Proto–Oncogene," *UMI Dissertation Services*, Oct. 1989.

Lee et al., "Molecular Basis of Tumor Suppression by the Human Retinoblastoma Gene," *Journal of Cellular Biochemistry*, UCLA Symposia on Molecular & Cellular Biology, Abstracts, 19th Annual Meeting, Supplement 14C, Abstract No. I 001, Feb. 3–Mar. 11, 1990.
Levine et al., "The p53 Growth Suppressor Gene," *Journal of Cellular Biochemistry*, UCLA Symposia on Molecular & Cellular Biology, Abstracts, 19th Annual Meeting, Supplement 14C:264, Abstract No. I 029, Feb. 3–Mar. 11, 1990.
Mercer et al., "Antiproliferative Effects of Wild Type Human P53," *Journal of Cellular Biochemistry*, UCLA Symposia on Molecular & Cellular Biology, Abstracts, 19th Annual Meeting, Supplement 14C:264, Abstract No. I 224, Feb. 3–Mar. 11, 1990.
Minna et al., "The Molecular Pathogenesis of Lung Cancer Involves the Accumulation of a Large Number of Mutations in Dominant Oncogenes and Multiple Tumor Suppressor Genes (Recessive Oncogenes)," *Journal of Cellular Biochemistry*, UCLA Symposia on Molecular & Cellular Biology, Abstracts, 19th Annual Meeting, Supplement 14C:264, Abstract No. I 003, Feb. 3–Mar. 11, 1990.
Vogelstein et al., "Genetic Alterations Accumulate During Colorectal Tumorigenesis," *Journal of Cellular Biochemistry*, UCLA Symposia on Molecular & Cellular Biology, Abstracts, 19th Annual Meeting, Supplement 14C:264, Abstract No. I 004, Feb. 3–Mar. 11, 1990.
Davidson et al., "A Model System for In Vivo Gene Transfer into the Central Nervous System Using an Adenoviral Vector," *Nature Genetics*, 3:219–223, Mar. 1993.
Anderson and Stanbridge, "Tumor Suppressor Genes Studied by Cell Hybridization and Chromosome Transfer," *The FASEB Journal*, 7:826–833, Jul. 1993.
Baker et al., "Suppression of Human Colorectal Carcinoma Cell Growth by Wild–Type p53," *Science*, 249:912–915, Aug. 1990.
Baker et al., "Chromosome 17 Deletions and p53 Gene Mutations in Colorectal Carcinomas," *Science*, 244:217–221, Apr. 1989.
Bartel and Szostak, "Isolation of New Ribozymes from a Large Pool of Random Sequences," *Science* 261:1411–1418, Sep. 1993.
Beaudry and Joyce, "Directed Evolution of an RNA Enzyme," *Science*, 257:635–641, Jul. 1992.
Belani, "Multimodality Management of Regionally Advanced Non–Small–Cell Lung Cancer," *Seminars in Oncology*, 20(4):302–314, Aug. 1993.
Bishop, "The Molecular Genetics of Cancer," *Science*, 235:305–311, Jan. 1987.

(List continued on next page.)

Primary Examiner—John L. LeGuyader
(74) Attorney, Agent, or Firm—Fulbright & Jaworski

(57) ABSTRACT

The present invention discloses expression constructs and methods for employing them that result in the modulation of abnormal oncogene and tumor suppressor genes in a novel approach to cancer prevention and therapy. In one embodiment, an expression construct expresses a ribozyme that inactivates mutant p53 and also expresses the functional p53.

25 Claims, 7 Drawing Sheets

OTHER PUBLICATIONS

Boussif et al., "A Versatile Vector for Gene and Oligonucleotide Transfer Into Cells in Culture and in vivo: Polyethylenimine," *Proc Natl Acad Sci, USA,* 92:7297–7301, Aug. 1995.

Breaker and Joyce, "A DNA Enzyme That Cleaves RNA," *Chemistry & Biology,* 1(4):223–229, 1994.

Cai et al., "Stable Expression of the Wild–Type p53 Gene in Human Lung Cancer Cells After Retrovirus–Mediated Gene Transfer," *Human Gene Therapy,* 4:617–624, 1993.

Cai et al., "Suppression of Lung Cancer Cell Growth by Ribozyme–Mediated Modification of p53 Pre–mRNA," *Cancer Gene Therapy,* 2(3):199–205, 1995.

Casey et al., "Growth Suppression of Human Breast Cancer Cells by the Introduction of a Wild–Type p53 Gene," *Oncogene,* 6:1791–1797, 1991.

Casson et al., "p53 Gene Mutations in Barrett's Epithelium and Esophageal Cancer," *Cancer Research,* 51:4495–4499, Aug. 1991.

Chen et al., "Genetic Mechanisms of Tumor Suppression by the Human p53 Gene," *Science,* 250:1576–1580, Dec. 1990.

Coupar et al., "A General Method for the Construction of Recombinant Vaccinia Viruses Expressing Multiple Foreign Genes," *Gene,* 68:1–10, 1988.

Culver et al., In vivo Gene Transfer with Retroviral Vector––Producer Cells for Treatment of Experimental Brain Tumors, *Science,* 256:1550–1552, Jun. 1992.

Dai et al., "Cleavage of an Amide Bond by a Ribozyme," *Science,* 267:237–240, Jan. 1995.

Denman and Miller, "Novel Cleavage of a Hammerhead Ribozyme Targeted to β–Amyloid Peptide Precursor mRNA," *Archives of Biochemistry and Biophysics,* 305(2):392–400, Sep. 1993.

Diller et al., "p53 Functions as a Cell Cycle Control Protein in Osteosarcomas," *Molecular and Cellular Biology,* 10(11):5772–5781, Nov. 1990.

Eliyahu et al., "Participation of p53 Cellular Tumour Antigen in Transformation of Normal Embryonic Cells," *Nature,* 312:646–649, Dec. 1984.

Forster and Symons, "Self–Cleavage of Plus and Minus RNAs of a Virusoid and a Structural Model for the Active Sites," *Cell,* 49:211–220, Apr. 1987.

Friedmann, "Progress Toward Human Gene Therapy," *Science,* 244:1275–1281, Jun. 1989.

Fujiwara et al., "Therapeutic Effect of a Retroviral WildType p53 Expression Vector in an Orthotopic Lung Cancer Model," *Journal of the National Cancer Institute,* 86(19)1458–1462, Oct. 1994.

Georges et al., "Prevention of Orthotopic Human Lung Cancer Growth by Intratrachael Instillation of a Retroviral Antisense K–ras Construct," *Cancer Research,* 53:1743–1746, Apr. 1993.

Gerlach et al., "Construction of a Plant Disease Resistance Gene from the Satellite RNA of Tobacco Ringspot Virus," *Nature,* 328:802–805, Aug. 1987.

Ghosh and Bachhawat, "Targeting of Liposomes to Hepatocytes," In:*Liver Diseases: Targated Diagnosis and Therapy Using Specific Receptors and Ligands,* Wu and Wu (Eds), Chapter 4, pp. 87–103, Marcel Dekker, Inc., New York, NY, 1991.

Gould and Warren, "Epithelial Neoplasms of the Lung," In:*Thoracic Oncology,* Chapter 6, pp. 77–93, Roth, Ruckdeschel & Weisenburger (Eds) W.B. Saunders Company, 1989.

Goyette et al., "Progression of Colorectal Cancer is Associated with Multiple Tumor Suppressor Gene Defects but Inhibition of Tumorigenicity is Accomplished by Correction of Any Single Defect Via Chromosome Transfer," *Molecular and Cellular Biology,* 12(3):1387–1395, Mar. 1992.

Green and Szostak, "Selection of a Ribozyme That functions as a Superior Template in a Self–Copying Reaction," *Science,* 258:1910–1915, Dec. 1992.

Grunhaus and Horwitz, "Adenoviruses as Cloning Vectors," *Seminars in Virology,* 3:237–252, 1992.

Herz and Gerard, "Adenovirus–Mediated Transfer of Low Density Lipoprotein Receptor Gene Acutely Accelerates Cholesterol Clearance in Normal Mice," *Proc Natl Acad Sci, USA,* 90:2812–2816, Apr. 1993.

Hesdorffer et al., "Efficient Gene Transfer in Live Mice Using a Unique Retroviral Packaging Line," *DNA and Cell Biology,* 9(10):717–723, 1990.

Hinds et al., Mutation is Required to Activate the p53 Gene for Cooperation with the ras Oncogene and Transformation, *Journal of Virology,* 63(2):739–746, Feb. 1989.

Hollstein et al., "p53 Mutations in Human Cancers," *Science,* 253:49–53, Jul. 1991.

Iverson, "Ribozymes, Recognition and Evolution," *Chemistry & Biology,* 2(2):67–70, May 1995.

Jenkins et al., "Cellular Immortalization by a cDNA Clone Encoding the Transformation–Associated Phosphoprotein p53," *Nature,* 312:651–654, Dec. 1984.

Joyce, "RNA Evolution and the Origins of Life," *Nature,* 338:217–224, Mar. 1989.

Kashani–Sabet et al., "Reversal of the Malignant Phenotype by an Anti–ras Ribozyme," *Antisense Research and Development,* 2:3–15, 1992.

Kim and Cech, "Three–Dimensional Model of the Active Site of the Self–Splicing rRNA Precursor of Tetrahymena," *Proc Natl Acad Sci, USA,* 84:8788–8792, Dec. 1987.

Lane and Benchimol, "p53: Oncoggene or Anti–Oncogene?" *Genes & Development,* 4:1–8, 1990.

Lehman and Joyce, "Evolution in vitro of an RNA Enzyme With Altered Metal Dependence," *Nature,* 361:182–185, Jan. 1993.

Lerner et al., "At the Crossroads of Chemistry and Immunology: Catalytic Antibodies," *Science,* 252:659–667, May 1991.

Lorsch and Szostak, "In vitro Evolution of new Ribozymes With Polynucleotide Kinase Activity," *Nature,* 371:31–36, Sep. 1994.

McCall et al., "Minimal Sequence Requirements for Ribozyme Activity," *Proc Natl Acad Sci, USA,* 89:5710–5714, Jul. 1992.

Mercer et al., "Negative Growth Regulation in a Glioblastoma Tumor Cell Line That Conditionally Expresses Human Wild–Type p53," *Proc Natl Acad Sci, USA,* 87:6166–6170, Aug. 1990.

Michalovitz et al., "Conditional Inhibition of Transformation and of Cell Proliferation by a Temperature–Sensitive Mutant of p53," *Cell,* 62:671–680, Aug. 1990.

Michel and Westhof, "Modelling of the Three–Dimensional Architecture of Group I Catalytic Introns Based on Comparative Sequence Analysis," *Journal of Molecular Biology,* 216:585–610, 1990.

Mitsudomi et al., "p53 Gene Mutations in Non–Small–Cell Lung Cancer Cell Lines and Their Correlation With the Presence of ras Mutations and Clinical Features," *Oncogene,* 7:171–180, 1992.

Mukhopadhyay and Roth, "A Codon 248 p53 Mutation Retains Tumor Suppressor Function as Shown by Enhancement of Tumor Growth by Antisense p53," *Cancer Research,* 53:4362–4366, Sep. 1993.

Mukhopadhyay et al., "Specific Inhibition of K–ras Expression and Tumorigenicity of Lung Cancer Cells by Antisense RNA," *Cancer Research,* 51:1744–1748, Mar. 1991.

Mulligan, "The Basic Science of Gene Therapy," *Science,* 260:926–932, May 1993.

Nicolau et al., Liposomes as Carriers for in vivo Gene Transfer and Expression, *Methods in Enzymology,* 149:157–177, 1987.

Nigro et al., "Mutations in the p53 Gene Occur in Diverse Human Tumour Types," *Nature,* 342:705–708, Dec. 1989.

Osborne and Miller, "Design of Vectors for Efficient Expression of Human Purine Nucleoside Phosphorylase in Skin Fibroblasts from Enzyme–Deficient Humans," *Proc Natl Acad Sci, USA,* 85:6851–6855, Sep. 1988.

Pan and Uhlenbeck, "In vitro Selection of RNAs That Undergo Autolytic Cleavage With $Pb^{2+}$," *Biochemistry,* 31(16):3887–3895, Apr. 1992.

Parada et al., "Cooperation Between Gene Encoding p53 Tumour Antigen and ras in Cellular Transformation," *Nature,* 312:649–651, Dec. 1984.

Perriman et al., "Extended Target–Site Specificity for a Hammerhead Ribozyme," *Gene,* 113:157–163, 1992.

Prudent et al., "Expanding the Scope of RNA Catalysis," *Science,* 264:1924–1927, Jun. 1994.

Putnam et al., "Autocrine Growth Stimulation by Transforming Growth Factor–α in Human Non–Small Cell Lung Cancer," *Surgical Oncology,* 1:49–60, 1992.

Reihsaus et al., "Regulation of the Level of the Oncoprotein p53 in Non–Transformed and Transformed Cells," *Oncogene,* 5:137–145, 1990.

Reinhold–Hurek and Shub, "Self–Splicing Introns in tRNA Genes of Widely Divergent Bacteria," *Nature,* 357:173–176, May 1992.

Renan, "Cancer Genes: Current Status, Future Prospects, and Applications in Radiotherapy/Oncology," *Radiotherpay and Oncology,* 19:197–218, 1990.

Rich et al., "Development and Analysis of Recombinant Adenoviruses for Gene Therapy of Cystic Fibrosis," *Human Gene Therapy,* 4:461–476, 1993.

Rippe et al., "DNA–Mediated Gene Transfer Into Adult Rat Hepatocytes in Primary Culture," *Molecular and Cellular Biology,* 10(2):689–695, Feb. 1990.

Roth et al., "A Randomized Trial Comparing Perioperative Chemotherapy and Surgery With Surgery Alone in Resectable Stage IIIA Non–Small–Cell Lung Cancer," *Journal of the National Cancer Institute,* 86(9):673–680, May 1994.

Ruffner et al., "Sequence Requirements of the Hammerhead RNA Self–Cleavage Reaction," *Biochemistry,* 29:10695–10702, 1990.

Sarver et al., "Ribozymes as Potential Anti–HIV–1 Therapeutic Agents," *Science,* 247:1222–1225, Mar. 1990.

Scanlon et al., "Ribozyme–Mediated Cleavage of c–fos mRNA Reduces Gene Expression of DNA Synthesis Enzymes and Metallothionein," *Proc Natl Acad Sci, USA,* 88:10591–10595, Dec. 1991.

Sioud et al., "Preformed Ribozyme Destroys Tumour Necrosis Factor mRNA in Human Cells," *Journal of Molecular Biology,* 223:831–835, 1992.

Suzuki et al., "p53 Mutations in Non–Small Cell Lung Cancer in Japan: Association Between Mutations and Smoking," *Cancer Research,* 52:734–736, Feb. 1992.

Takahashi et al., "Wild–Type But Not Mutant p53 Suppresses the Growth of Human Lung Cancer Cells Bearing Multiple Genetic Lesions," *Cancer Research,* 52:2340–2343, Apr. 1992.

Takahashi et al., "p53: A Frequent Target for Genetic Abnormalities in Lung Cancer," *Science,* 246:491–494, Oct. 1989.

Tang et al., "In vivo Catalysis of a Metabolically Essential Reaction by an Antibody," *Proc Natl Acad Sci, USA,* 88:8784–8786, Oct. 1991.

Travali et al., "Oncogenes in Growth and Development," *The FASEB Journal,* 4:3209–3214, Nov. 1990.

Tsang and Joyce, "Evolutionary Optimization of the Catalytic Properties of a DNA–Cleaving Ribozyme," *Biochemistry,* 33:5966–5973, 1994.

Wagner et al., "Antisense Gene Inhibition by Oligonucleotides Containing C–5 Propyne Pyrimidines," *Science,* 260:1510–1513, Jun. 1993.

Weinberg, "Tumor Suppressor Genes," *Science,* 254:1138–1146, Nov. 1991.

Wu and Wu, "Liver–Directed Gene Delivery," *Advanced Drug Delivery Reviews,* 12:159–167, 1993.

Yang et al., "In vivo and in vitro Gene Transfer to Mammalian Somatic Cells by Particle Bombardment," *Proc Natl Acad Sci USA,* 87:9568–9572, Dec. 1990.

Yuan and Altman, "Selection of Guide Sequences That Direct Efficient Cleavage of mRNA by Human Ribonuclease P," *Science,* 263:1269–1273, Mar. 1994.

Zakut–Houri et al., "Human p53 Cellular Tumor Antigen: cDNA Sequence and Expression in COS Cells," *The EMBO Journal,* 4(5):1251–1255, 1985.

* cited by examiner

```
                         SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:1:

CAAGATGGAT TGCACGCAGG                                              20

(2) INFORMATION FOR SEQ ID NO:2:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:2:

CCCGCTCAGA AGAACTCGTC                                              20

(2) INFORMATION FOR SEQ ID NO:3:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:3:

TCTGACTGTA CCACCATCCT                                              20

(2) INFORMATION FOR SEQ ID NO:4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "DNA"

(xi) SEQUENCE DESCRIPTION: SEQ ID NO:4:

CTGGAGTCTT CCAGTGTGAT                                              20
```

```
(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:5:

GATGGGCCTC CGGTTCATGC C                                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:6:

GATGGGCCTC AGGTTCATGC C                                              21

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:7:

TCTGACTGTA CCACCATCCA                                                20

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:8:

ACCTGCAGCC CAAGCTTCGA G                                              21

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:9:

TGCAAGTCAC AGACTTGGCT G                                              21
```

(2) INFORMATION FOR SEQ ID NO:10:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:10:

```
TAATACGACT CACTATAGGG CGAATTCGCT GAGGAGGGGC CACTGATCAG T          51
```

(2) INFORMATION FOR SEQ ID NO:11:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:11:

```
GGATCCGATT GCTCTTAGGT TTCGTCCAAA AGGACTCATC AGTGG              45
```

(2) INFORMATION FOR SEQ ID NO:12:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:12:

```
GGATCCGATT GCTCTTAGGT CTCGTCCAAA AGGACTCATC AGTGG              45
```

(2) INFORMATION FOR SEQ ID NO:13:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:13:

```
TAATACGACT CACTATAGGG CGAATTCTCC GTCCCAGTAG ATCTGATG           48
```

(2) INFORMATION FOR SEQ ID NO:14:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:14:

```
TCCGGATCCT GAGTAGTGGT TTCGTCCAAA AGGACTCATC AGATCTAC           48
```

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:15:

CCTGAGGAGG GGCCACTGAT GAGTCCTTTT G                          31

(2) INFORMATION FOR SEQ ID NO:16:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:16:

TGATTGCTCT TAGGTTTCGT CCAAAAGGAC TCA                        33

(2) INFORMATION FOR SEQ ID NO:17:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:17:

TGATTGCTCT TAGGTCTCGT CCAAAAGGAC TCA                        33

(2) INFORMATION FOR SEQ ID NO:18:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:18:

TCCTGAGTAG TGGTTTCGTC CAAAAGGACT CAT                        33

(2) INFORMATION FOR SEQ ID NO:19:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:19:

```
CCTTCCCAGT AGATCTGATG AGTCCTTTTG GAC                              33

(2) INFORMATION FOR SEQ ID NO:20:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:20:

TAATACGACT CACTATAGGG CGAATTCCAC TGATTGCTCT TAGGTCTGGC CCCTCCT     57

(2) INFORMATION FOR SEQ ID NO:21:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:21:

GGATCCACAC GCAAATTTCC TTCCACTCGG ATAAGATGCT GAGGAGGGGC CAGA        54

(2) INFORMATION FOR SEQ ID NO:22:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:22:

TAATACGACT CACTATAGGG CGAATTCTGC TCAGATAGCG ATGGTCTGGC CCCTCCT     57

(2) INFORMATION FOR SEQ ID NO:23:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:23:

TAATACGACT CACTATAGGG CGAATTCCCT ATCCTGAGTA GTGGTAATCT ACTGGGA     57

(2) INFORMATION FOR SEQ ID NO:24:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:24:
```

CTCCGGATCC AGGCACAAAC ACGCACCTCA AAGCTGTTCC GTCCCAGTAG ATTACCA    57

(2) INFORMATION FOR SEQ ID NO:25:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:25:

TACTCCCCTG CCCTCAACAA G    21

(2) INFORMATION FOR SEQ ID NO:26:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:26:

CTTAGTGCTC CCTGGGGGCA G    21

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:27:

CTATTCCAGA AGTAGTGAGG A    21

(2) INFORMATION FOR SEQ ID NO:28:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

(xi) SEQUENCE DESCRIPTION: SEQ ID NO:28:

TCGTCCAAAA GGACTCATCA G    21

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "DNA"

```
                                       -continued (xi) SEQUENCE DESCRIPTION: SEQ ID NO:29:

GGGAGAAAAC GTTAGGGTGT G                                                    21
```

MODIFICATION OF MUTATED P53 GENE IN TUMORS BY RETROVIRAL DELIVERY OF RIBOZYME A

The government may own certain rights in the present invention pursuant to grant number CA45187 from the National Cancer Institute.

BACKGROUND OF THE INVENTION

Cancer constitutes one of the greatest health threats in the world, responsible for over one-half million deaths each year in the U.S. alone. Unfortunately, current treatment methods for cancer, including radiation therapy, surgery, and chemotherapy, are known to have limited effectiveness. For example, non-small-cell lung cancer ("NSCLC"), which includes squamous cell carcinoma, adenocarcinoma and large-cell carcinoma, accounts for 75%–80% of all lung cancers (Gould & Warren, 1989). Multimodality therapeutic strategies have been applied to regionally advanced NSCLC but the overall cure rate, which is approximately 10%, remains unsatisfactory (Belani, 1993; Roth et al., 1994).

Increased understanding of the molecular pathogenesis of cancer has profoundly changed the view of the pathogenesis of the disease, as the development of cancer is considered to result from multiple genetic alterations (Goyette et al., 1992; Klein et al., 1987). It now is well established that a variety of cancers are caused, at least in part, by genetic abnormalities that result in either the overexpression of one or more genes, or the expression of an abnormal or mutant gene or genes. For example, in many cases, the expression of oncogenes is known to result in the development of cancer. "Oncogenes" are defined as genetically altered genes whose mutated expression product somehow disrupts normal cellular function or control (Spandidos at al., 1989). From melanomas to lymphomas, these mutations are believed to effect the neoplastic growth of cells derived from every tissue.

Most oncogenes studied to date have been found to be "activated" as the result of a mutation, often a point mutation, in the coding region of a normal cellular gene, i.e., a "proto-oncogene". The mutation results in amino acid substitutions in the expressed protein product. This altered expression product exhibits an abnormal biological function that takes part in the neoplastic process. The underlying mutations can arise by various means, such as by chemical mutagenesis or ionizing radiation. A number of oncogenes and oncogene families, including ras, myc, neu, raf, erb, src, fms, jun and abl, have now been identified and characterized to varying degrees (Travali et al., 1990; Bishop, 1987).

Another gene of interest involved in the regulation of cell growth is the tumor suppressor p53. Mutations of the p53 gene span several coding regions and are the most common yet described for human cancer (Hollstein et al., 1991; Lane & Benchimol, 1990). These mutations not only eliminate the tumor suppressor activity but also stimulate growth of malignancies. In addition, the mutant p53 protein may possess transforming ability and can cooperate with other oncogenes in the transformation of normal cells (Parada et al., 1984; Jenkins et al., 1984; Elihayu et al., 1984; Hinds et al., 1989). The mutant p53 protein also has a prolonged half-life of 2 to 12 hours, resulting in higher intracellular concentrations than the wild-type protein (Reihsaus et al., 1990). Loss of the ability to suppress transformation and gain of transforming potential are properties of the mutant p53 gene product.

Importantly, the malignant phenotypes of certain cancer cells can be reversed by the introduction of a recombinant construct that reverses a single genetic lesion, a single normal cell-derived chromosome, or a copy of a wild-type tumor suppressor gene (Goyette et al., 1992; Takahashi et al., 1992; Anderson & Stanbridge, 1993; Mukhopadhyay et al., 1991). This finding suggests that correction of a single oncogene or tumor suppressor gene abnormality may overcome the effect of multiple genetic changes in the cancer cell (Goyette et al., 1992; Takahashi et al., 1992; Anderson & Stanbridge, 1993; Mukhopadhyay et al., 1991). It also may be desirable to develop enzymes that inactivate a particular oncogene.

Although proteins traditionally have been targeted for biological catalysis or enzyme mimics, other biological macromolecules, such as RNA molecules (commonly known as "ribozymes"), are also capable of accelerating chemical transformations. Ribozymes may be particularly promising because many of these enzymes have a specific catalytic domain that possesses endonuclease activity (Kim & Cech, 1987; Gerlach et al., 1987; Forster & Symons, 1987). For example, a large number of ribozymes accelerate phosphoester transfer reactions with a high degree of specificity often cleaving only one of several phosphoesters in an oligonucleotide substrate (Cech et al., 1981; Michel & Westhof, 1990; Reinhold-Hurek & Shub, 1992). This specificity has been attributed to the requirement that the substrate bind via specific base-pairing interactions to the internal guide sequence ("IGS") of the ribozyme prior to chemical reaction.

Despite the broad range of chemical functionalities present within RNA, ribozyme catalysis mainly has been limited to sequence specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Ribozyme-mediated inhibition of gene expression may be particularly useful in therapeutic applications if the catalytic sequence can be designed to cleave a specific target RNA sequence (Scanlon et al., 1991; Sarver et al., 1990; Sioud et al., 1992).

Recently, it was reported that ribozymes elicited genetic changes in some cell lines to which they were applied; the altered gene included H-ras, c-fos, and genes of HIV virus. Most of this work involved the modification of mRNA based on a specific mutant codon that is cleaved by a specific ribozyme.

Despite these advances, there remains a need for improved methods of using ribozymes in the treatment of malignant cells. In particular, there is a need for specific application of ribozyme-mediated intervention in p53 transformation of human cancer cells.

SUMMARY OF THE INVENTION

It is, therefore, a goal of the present invention to provide compositions and methods relating to the control of oncogenesis as it relates to cancer cells having transforming mutations in the p53 gene. While conventional gene replacement therapy may be sufficient in certain situations, e.g., where the p53 mutant simply has lost tumor suppressing activity, it may not suffice in others where the altered p53 actively contributes to the malignant phenotype. In such a case, it will be desirable to inactivate the mutant gene while, at the same time, restoring normal p53 function. The present invention seeks to provide gene therapeutic constructs and methods that inactivate a mutant p53 and also provide for restoration of wild-type p53 function.

This invention generally relates to expression constructs that express a ribozyme that inactivates pre-mRNA of the mutant p53 and methods for their use. More specifically, the present invention provides a retroviral vector-mediated system that can be used to transduce various hammerhead ribozymes into cancer cells, such as human lung cancer cells.

This invention also relates to the design of ribozymes that will interrupt the pre-mRNA splicing process of p53 transcripts. An advantage of this method for modifying pre-mRNA is that joint sequences between introns and exons can be used to develop ribozyme target sequences. Such a ribozyme cleaves the target sequence and interrupts the process of splicing from pre-mRNA to mRNA. At the same time, the ribozyme would not affect a cDNA provided to the same cell.

It also is contemplated, as part of the present invention, to provide a replacement p53 gene that exhibits wild-type p53 activity. This replacement gene is engineered to avoid the action of the ribozyme, for example, by being provided in the form of a cDNA or a construct otherwise lacking the ribozyme target.

In one embodiment of the present invention, an expression construct is provided comprising a first promoter functional in eukaryotic cells and a first nucleic acid encoding a p53-specific ribozyme, where the first nucleic acid is under transcriptional control of the first promoter. Preferred embodiments of this aspect of the invention include a retrovirus promoter or an SV40 promoter being most preferred. In a specific embodiment, the ribozyme of the expression construct targets a p53 intron-exon splice junction, particularly the p53 codon 187.

In another embodiment of the present invention, an expression construct further codes for a second nucleic acid, preferably a cDNA, encoding a functional p53, where the second nucleic acid transcript is not cleaved by the ribozyme. As used herein the term "second nucleic acid transcript" refers to the wt-p53 mRNA that is expressed by the construct and encoded by the second nucleic acid. The second nucleic acid transcript is not cleaved because the ribozyme specifically cleaves a target site absent from that transcript. In certain applications, it may be preferable to have the second nucleic acid under the transcriptional control of a second, separate promoter which also is functional in eukaryotic cells.

In another embodiment of the present invention there is provided a pharmaceutical composition comprising (i) an expression construct comprising a first promoter functional in eukaryotic cells and a first nucleic acid encoding a p53-specific ribozyme, where the first nucleic acid is under transcriptional control of said first promoter and (ii) a pharmaceutically acceptable buffer, solvent or diluent. It may be preferable to have the expression construct further comprise a second nucleic acid encoding a functional p53, wherein the second nucleic acid transcript is not cleaved by the ribozyme. It also may be preferable to have the expression construct further comprise a second promoter functional in eukaryotic cells, wherein the second nucleic acid is under the transcriptional control of the second promoter.

In yet another embodiment, the present invention encompasses a method for inhibiting mutant p53 function in a cell comprising the steps of (i) providing an expression construct comprising a promoter functional in eukaryotic cells and a nucleic acid encoding a p53-specific ribozyme, where the nucleic acid is under transcriptional control of the promoter; and (ii) contacting the expression construct with the cell.

A preferred expression construct of the present invention is a retrovirus. It is also preferred to have the ribozyme target a p53 intron-exon splice junction, particularly the p53 codon 187.

A further embodiment of the present invention includes a method for restoring p53 function to a cell lacking a functional p53 comprising the steps of (i) providing a first expression construct comprising a first promoter functional in eukaryotic cells and a first nucleic acid encoding a p53-specific ribozyme, where the first nucleic acid is under transcriptional control of the first promoter; (ii) providing a second expression construct comprising a second promoter functional in eukaryotic cells and a second nucleic acid encoding a functional p53 lacking the target site for the p53-specific ribozyme, where the second nucleic acid is under transcriptional control of the second promoter and the second nucleic acid transcript is not cleaved by the ribozyme; and (iii) contacting the first and the second expression constructs with the cell.

Particular embodiments of the present invention are provided for restoring p53 function to a cell lacking a functional p53 utilizing retrovirus expression constructs.

Also provided are methods for treating a mammal with cancer comprising the steps of (i) identifying a mammal having a cancer characterized by cells expressing a mutated, transforming p53 product; (ii) providing an expression construct, preferably a retrovirus containing a first promoter functional in eukaryotic cells and a first nucleic acid encoding a p53-specific ribozyme, where the first nucleic acid is under transcriptional control of the first promoter and a second nucleic acid encoding a functional p53 lacking the target site for the p53-specific ribozyme, preferably a cDNA, wherein the second nucleic acid transcript is not cleaved by said ribozyme; and (iii) contacting the expression construct with the cells.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A. H460a cell line. LNSX/p53(a):LNSX (○), vector alone (●). For growth rate analysis, p53 transduced and nontransduced cells were plated in triplicate (10⁴ cells per well), and cells from three wells were counted each day for 7 days. The mean±SE is shown.

FIG. 6B. Transduced cells used for growth analysis were infected twice with fresh 0.5 ml of viral supernate and 8 µg/ml of Polybrene for 2 consecutive days before plating. H322a cell line: H322a-LNSX/p53(a) (○), H322a-LNSX (▲), and H322a-LNSX/mutated p53 (Δ). For subsequent studies, cells were selected in G418 after transduction.

FIG. 6C. H358 cell line. H358a-LNSX/p53(a) (▲), H358a cells were mixed with H358a-LNSX/p53(a) at a ratio of 1:1 (○), H358a cells transduced with LNSX/mutated p53 (66 ), and H358a (●).

FIG. 6D. H460a cell line. H460a-LNSX/p53(a) (○), H460a-LNSX (●), and H460a (Δ).

FIG. 6E. H322a cell line. H322a-LNSX/p53(a) (●), H322a cells mixed with H322a-LNSX/p53(a) cells at a ratio of 1:1 (Δ), and H322a (▲).

FIG. 6F. Growth rate of H322a cell line after incubation with supernate of p53 transduced H322a cells. H322a cells (10⁴) were seeded in 12-well plates, and supernate of H322a cells was replaced either by supernate of H322a-LNSX/p53 (a), H322a-LNSX, or H460a every day for 7 days. Growth rate was calculated as described above.

FIG. 7. Densitometric analysis of autoradiographs from western blot analysis. Lane 1, H226Br; lane 2, H226Br-LNSRz5m; lane 3, H226Br-LNSRz7a; lane 4, H226Br-LNSRz5a.

DETAILED DESCRIPTION OF THE PREFERRED EMBODIMENTS

Figure 1:
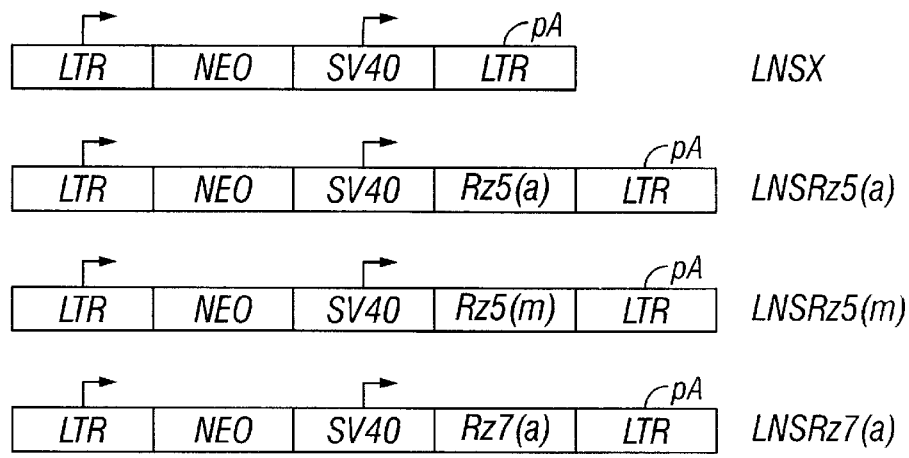
FIG. 1. Construction of the retroviral vectors. Arrows indicate the direction of long terminal repeat ("LTR") and SV40 promoter transcription; pA indicates polyadenylation signals.

The present invention generally relates to an expression construct for both a functional p53 and a ribozyme that inactivates mutant p53 mRNA. In one embodiment, the ribozyme targets only pre-mRNA. This permits a replacement p53 introduced into the same cell to compensate for the missing tumor suppressing activity while avoiding the action of the ribozyme produced by the vector. Thus, the mutant form of p53 is inactivated and the wild-type form is restored to the cell. While it may generally be preferred to have an expression construct that both expresses functional p53 and inactivates mutant p53 pre-mRNA, it is contemplated that expression constructs that only inactivate mutant p53 pre-mRNA also will be useful.

Recent advances in the understanding of pre-mRNA splicing have made it possible to design ribozymes that will interrupt the pre-mRNA splicing process. An advantage of this new method for modifying pre-mRNA is that joint sequences between introns and exons can be selected for developing the ribozyme's target sequence. The ribozyme cleaves the target sequence and interrupts the process of splicing from pre-mRNA to mRNA, preventing the synthesis of the abnormal protein.

Moreover, the relatively small size of the ribozymal RNA should not present any problems in terms of the retroviral construct's capacity to carry foreign coding sequences. It also is expected that recombinant retrovirus vectors encoding ribozymes will show normal viral particle production and have high infection efficiency. It also is contemplated that, while the present invention is exemplified by the use of a ribozyme directed against p53, the principle may be used to target virtually any dominant mutant gene defect responsible for disease.

A. Nucleic Acids

Nucleic acids include both deoxyribonucleic acids (DNAs) and ribonucleic acids (RNAs). For DNAs, both cDNA and genomic sequences are suitable for eukaryotic expression. As used herein, the term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA does not contain internal non-coding sequences but, rather, contains an uninterrupted coding region for the corresponding protein. There may be times when the full or partial genomic sequence is preferred, however (Sambrook et al., 1989).

1. Ribozymes

The term "ribozyme", as used herein, refers to an RNA-based enzyme capable of targeting and cleaving particular base sequences in nucleic acids. Ribozymes can either be targeted directly to cells, in the form of preformed RNA molecules incorporating ribozyme sequences, or introduced into the cell in the form of a DNA expression construct that encodes the desired ribozymal RNA.

Ribozymes are used and applied using many of the same principles as antisense nucleic acids. Ribozymes rely on complementary binding to nucleic acids for target recognition. Nucleic acid sequences which comprise "complementary nucleotides" are those which are capable of base-pairing according to the standard Watson-Crick complementarity rules. That is, that the larger purines will base pair with the smaller pyrimidines to form combinations of guanine paired with cytosine (G:C) and adenine paired with either thymine (A:T), in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

As mentioned previously, the majority of reactions catalyzed by ribozymes involve ligation and cleavage of nucleic acids. However, the list of reactions catalyzed by RNA was expanded when Piccirilli et al. (1992) showed that the Tetrahymena group I intron could accelerate the hydrolysis of a carboxyester appropriately placed within an oligonucleotide substrate.

Ribozymes that modulate oncogene expression have been reported previously. These include a ribozyme specifically targeting a mutant oncogene codon in which the mutation was suitable for ribozyme activity (Kashani-Sabet et al., 1992). Another study showed that pre-mRNA can be modified by a specific ribozyme in vitro (Denman & Miller, 1993). The inventors believe, however, that this is the first report of modification of p53 pre-mRNA by a ribozyme. Because mutations in the p53 gene may occur at many different sites, and many tumors have a p53 deletion associated with a mutation, targeting of the pre-mRNA provides a technique for reducing expression of the endogenous mutant p53 by using a single construct.

The ribozymes of the present invention have been developed to selectively modify p53 mRNA. For example, ribozymes are designed to target a specific mutated codon in p53 mRNA for cleavage. Alternatively, ribozymes of the present invention targeted to "native" sequences such as intron-exon splice sites of pre-mRNA that can be genetically engineered out of other, compensatory constructs. The results' disclosed in this application demonstrate that, using this latter approach, the ribozyme cleaves pre-mRNA but not mature RNA in vitro.

The normal ribozyme LNSRz5(a) and a mutated form LSNRz5(m) are useful for comparing effects in target cells after transduction. LNSRz5(a) targets p53 mRNA at codon 187 (GUC) by recognition of two flanking sequences complementary to the 3' terminus of intron 5 and the 5' end of exon 6. This ribozyme effectively cleaves p53 pre-mRNA, transcribed in vitro, but does not cleave p53 mRNA, which lacks the intron 5 sequences. The mutant ribozyme does not cleave p53 pre-mRNA or mRNA.

Northern and western blot analyses show that LNSRz5(a), but not LNSRz5(m), reduce expression of mutant p53 mRNA and protein in H226Br cells. LNSRz5(a), but not LNSRz5(m), also markedly inhibits proliferation of H226Br cells after infection. In contrast, a different ribozyme designated LNSRz7(a), targeting mutant p53 pre-mRNA at codon 262 (GUA) using two flanking sequences complementary to intron 7 and exon 8, does not reduce the rate of colony formation and does not inhibit p53 expression or proliferation. This indicates that any p53-directed ribozyme may not result in abrogation of the protein's activity.

A number of methods are available for the generation, amplification and selection of ribozymes with a desired activity. Prudent et al. (1994) have reported that transition state analog principles are applicable to the design of RNA-cleaving molecules. In employing the transition state analog concept, a molecule that resembles the predicted transition state for a bond isomerization is selected from an artificial library of RNA sequences based on their ability to bind the transition state analog species with high affinity. The selected molecules can then be amplified using the polymerase chain reaction ("PCR") and re-selected for the ability to bind the transition state analog covalently bound to a matrix. Prudent et al. (1994) reported that seven rounds of selection/amplification yielded an RNA sequence that exhibited a $k_{cat}/K_{uncat}$ value of 88 for the isomerization of a diastereomeric biphenyl compound.

Ribozymes with a desired activity also may be directly selected from a large ($>10^{12}$ molecules) randomized pool of RNA molecules on the basis of their ability to accelerate a chosen reaction (Green & Szostak, 1992; Beaudry & Joyce, 1992; Lehman & Joyce, 1993; Hartel & Szostak, 1993; Lorsch & Szostak, 1994; Tsang & Joyce, 1994; Pan & Uhlenbeck, 1992). Generally, the ribozyme is self-modified during the course of the reaction, and acceleration of the self-modification reaction enables the preferential PCR amplification of the active ribozyme. Using this type of selection scheme, ribozymes have been selected that function as improved templates in a self-copying reaction (Green & Szostak, 1992) and tRNA-derived molecules have also apparently been selected with an increased ability to undergo $Pb^{2+}$-dependent cleavage (Pan & Uhlenbeck, 1992). Using a similar procedure, Breaker & Joyce (1994) have reported the isolation of DNA sequences that accelerate the $Pb^{2+}$-dependent cleavage of a ribophosphoester embedded in a DNA molecule.

It is also contemplated that directed Darwinian evolution in vitro may be employed in the selection of ribozymes capable of functioning according to the present invention (Beaudry & Joyce, 1992; Lehman & Joyce, 1993; Hartel & Szostak, 1993; Lorsch & Szostak, 1994; Tsang & Joyce, 1994; Yuan & Altman, 1994; Dai et al., 1995). Using this approach, the acceleration of a chosen reaction is used in a selection scheme for the isolation and subsequent amplification of the desired RNA sequence. In this protocol, catalytically active RNA sequences are continually evolved in a Darwinian sense due to the limited random mutagenesis of the selected RNA sequence prior to each round of reaction-based selection.

Ribozymes generated by any of the above methods are expected to display sufficient specificity while performing the desired activity due to the required binding of substrate in the selection process.

2. p53 AND p53-Related Nucleric Acids

Throughout the application, the term "p53" is intended to refer to the exemplified p53 molecules as well as all p53 homologues from other species. "Functional" and "mutant" p53 refer, respectively, to a p53 gene expressing normal tumor suppressor activity and to a p53 gene lacking suppressor activity and/or having transforming activity. Thus, "mutant" p53's are not merely sequence variants but, rather, are those variants showing altered functional profiles.

The p53 gene encodes a 375-amino-acid phosphoprotein that can form complexes with regulatory proteins such as large-T antigen from SV40 and E1B from adenovirus. The protein is found in normal tissues and cells, but at concentrations which are minute by comparison to transformed cells or tumor tissue. Interestingly, functional p53 appears to be important in regulating cell growth and division. Overexpression of wild-type p53 has been shown in some cases to be anti-proliferative in human tumor cell lines. p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Although wild-type p53 is recognized as a centrally important growth regulator in many cell types, its genetic and biochemical traits appear to have a role as well. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey et al. (1991) have reported that transfection of DNA encoding wild-type p53 into two human breast cancer cell lines restores growth suppression control in such cells. A similar effect has also been demonstrated on transfection of wild-type, but not mutant, p53 into human lung cancer cell lines (Takahasi et al., 1992). The p53 appears dominant over the mutant gene and will select against proliferation when transfected into cells with the mutant gene. Normal expression of the transfected p53 does not affect the growth of cells with endogenous p53. Thus, such constructs might be taken up by normal cells without adverse effects.

The present invention contemplates the use of all p53 homologues. The same is true for p53-encoding nucleic acids. For nucleic acids, the variations may be purely genetic, i.e., ones that do not result in changes in the protein product. This includes nucleic acids that contain functionally equivalent codons, or codons that encode the same amino acid, such as the six codons for arginine or serine or codons that encode biologically equivalent amino acids (as in Table 1 below).

Alternatively, the changes in the p53 gene may give rise to changes in the p53 product itself. Because of the interactive capacity and nature of a protein, certain amino acid sequence substitutions can be made in a protein sequence (or, of course, its underlying nucleic acid coding sequence) and nevertheless obtain a protein with like (agonistic) properties. In order to function according to the present invention, all that is required is that a functional p53 express tumor suppressant activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It also is well understood by the skilled artisan that, inherent in the definition of a biologically functional equivalent protein, is the concept that there is a limit to the number of changes that may be made within a defined portion of the molecule and still result in a molecule with an acceptable level of equivalent biological activity. Biologically functional equivalent proteins are thus defined herein as those proteins in which certain, not most or all, of the amino acids may be substituted. A plurality of distinct polypeptides having various numbers of substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those which are within±1 are particularly preferred, and those within ±0.5 are even more particularly preferred.

It is understood that an amino acid can be substituted for another having a similar hydrophilicity value and still obtain a biologically equivalent protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5 ±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While the preceding discussion has focused on functionally equivalent polypeptides arising from amino acid changes, it will be appreciated that these changes may be effected by alteration of the encoding nucleic acid, taking into consideration also that the genetic code is degenerate and that two or more codons may code for the same amino acid.

B. Expression Constructs

The expression constructs of the present invention have the ability to both express a ribozyme that inactivates p53 pre-mRNA and also express a second, ribozyme resistant p53 mRNA. Throughout this application, the term "expression construct" is meant to include any type of genetic construct containing a nucleic acid coding for a gene product in which part or all of the nucleic acid encoding sequence is capable of being transcribed. The transcript may be translated into a protein, as in the case of a replacement construct, but it need not be, such as the ribozyme. In certain embodiments, expression includes both transcription of a p53 gene and translation of a p53 mRNA into a p53 gene product as well as the transcription of a p53-specific ribozyme while, in other embodiments, only the latter is contemplated.

1. Regulatory Elements

In preferred embodiments, the nucleic acid encoding a ribozyme and/or p53-derived product is under transcriptional control of one or more promoters. A "promoter" refers to a DNA sequence recognized by the synthetic machinery of the cell, or introduced synthetic machinery, required to initiate the specific transcription of a gene. Promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The phrase "under transcriptional control" means that the promoter is in the correct location and orientation in relation to the nucleic acid to control RNA polymerase initiation and expression of the gene. In general, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant RNA. This is the meaning of "recombinant expression" in this context. It also may be desirable to have the nucleic acids encoding the ribozyme and the wt-p53 mRNA be under the control of two separate promoters.

Promoters that are most commonly used in recombinant DNA construction include the β-galactosidase, β0-lactamase (penicillinase), lactose and tryptophan (trp) promoter systems. While these are the most commonly used, other promoters have been discovered and utilized, and details concerning their nucleotide sequences have been published, enabling those of skill in the art to ligate them functionally with plasmid vectors.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

The promoters may be derived from the genome of mammalian cells (e.g., metallothionein promoter) or from mammalian viruses (e.g., SV40 immediate early promoter; the adenovirus late promoter; the vaccinia virus 7.5K promoter, human cytomegalovirus (CMV) immediate early gene promoter, or Rous sarcoma virus long terminal repeat). Further, it is also possible, and may be desirable, to utilize promoter or control sequences normally associated with the desired gene sequence, provided such control sequences are compatible with the host cell systems.

The particular promoter that is employed to control the expression of a nucleic acid encoding a ribozyme or wt-p53 is not believed to be important, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

By employing a promoter with well-known properties, the level and pattern of expression of a ribozyme or p53 following transfection can be optimized. For example, selection of a promoter which is active specifically in lung cells, such as CC10 (lung tumor), will permit tissue-specific expression. Further, selection of a promoter that is regulated in response to specific physiologic signals can permit inducible expression. For example, with the nucleic acid encoding a ribozyme or p53 being expressed from the human PAI-1 promoter, expression is inducible by tumor necrosis factor. Tables 2 and 3 list several enhancers/promoters which may be employed, in the context of the present invention, to regulate the expression of a ribozyme or p53. This list is not intended to be exhaustive of all the possible elements involved in the promotion of expression but, merely, to be exemplary thereof.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a ribozyme or p53 in an expression construct (Table 2 and Table 3). Additionally any promoter/enhancer combination (as per the Eukaryotic Promoter Data Base EPDB) could also be used to drive expression. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression construct.

TABLE 2

ENHANCER

Immunoglobulin Heavy Chain
Immunoglobulin Light Chain
T-Cell Receptor
HLA DQ α and DQ β
β-Interferon
Interleukin-2
Interleukin-2 Receptor
MHC Class II $5_\alpha^k$
MHC Class II HLA-DRα
β-Actin
Muscle Creatine Kinase
Prealbumin (Transthyretin)
Elastase I
Metallothionein
Collagenase
Albumin Gene
α-Fetoprotein
τ-Globin
β-Globin
c-fos
c-HA-ras
Insulin
Neural Cell Adhesion Molecule (NCAM)
$\alpha_{1\text{-Antitrypsin}}$
H2B (TH2B) Histone
Mouse or Type I Collagen
Glucose-Regulated Proteins (GRP94 and GRP78)
Rat Growth Hormone
Human Serum Amyloid A (SAA)
Troponin I (TN I)
Platelet-Derived Growth Factor
Duchenne Muscular Dystrophy
SV40
Polyoma
Retroviruses
Papilloma Virus
Hepatitis B Virus
Human Immunodeficiency Virus
Cytomegalovirus
Gibbon Ape Leukemia Virus

TABLE 3

| Element | Inducer |
| --- | --- |
| MT II | Phorbol Ester (TFA) |
|  | Heavy metals |
| MMTV | Glucocorticoids |
| (mouse mammary tumor virus) |  |
| B-Interferon | poly(rI)X |
|  | poly(rc) |
| Adenovirus 5 E2 | Ela |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TFA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

In certain embodiments of the invention, the delivery of a nucleic acid in a cell may be identified in vitro or in vivo by including a marker in the expression construct. The marker would result in an identifiable change to the transfected cell permitting easy identification of expression. Usually the inclusion of a drug selection marker aids in cloning and in the selection of transformants. Alternatively, enzymes such as herpes simplex virus thymidine kinase (tk) may be employed. Immunologic markers also can be employed. The selectable marker employed is not believed to be important, so long as it is capable of being expressed simultaneously with the nucleic acid encoding a ribozyme or p53. Further examples of selectable markers are well known to one of skill in the art.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators (Bittner et al., 1987).

In eukaryotic expression, one will also typically desire to incorporate into the transcriptional unit an appropriate polyadenylation site (e.g., 5'-AATAAA-3') if one was not contained within the original cloned segment, particularly if using a cDNA insert. Typically, the poly A addition site is placed about 30 to 2000 nucleotides "downstream" of the termination site of the RNA. The nature of the polyadenylation signal is not believed to be crucial to the successful practice of the invention, and any such sequence may be employed. These elements can serve to enhance message levels and to minimize read through from the cassette into other sequences.

2. Vectors

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. This is accomplished by inserting the gene or genes of interest into a vector that is capable of transferring the inserted gene(s) into the host cell.

Many standard techniques are available to construct expression vectors containing the appropriate nucleic acids and transcriptional/translational control sequences in order to achieve RNA expression in a variety of host-expression systems. Cell types available for expression include, but are not limited to, GP+env Am12, yeast, mammalian, insect, and NIH-3T3 cells, transformed with vector DNA, such as phage, plasmid or cosmid.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells.

In preferred embodiments of the invention, the expression construct comprises a virus or engineered construct derived from a viral genome. The ability of certain viruses to enter cells via receptor-mediated endocytosis and express viral genes stably and efficiently have made them attractive candidates for the transfer of foreign genes into mammalian cells (Ridgeway, 1988; Nicolas & Rubenstein, 1988; Baichwal & Sugden, 1986; Temin, 1986). The first viruses used as gene vectors were DNA viruses including the papovaviruses (simian virus 40, bovine papilloma virus, and polyoma) (Ridgeway, 1988; Baichwal & Sugden, 1986) and adenoviruses (Ridgeway, 1988; Baichwal & Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kilobases of foreign genetic material but can be readily introduced in a variety of cell lines and laboratory animals (Nicolas & Rubenstein, 1988;

Temin, 1986).

a. Retroviruses

Retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene, termed Ψ, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a p53-specific ribozyme or a p53 is inserted into the viral genome in the place of certain viral sequences to produce a virus that is replication-defective. In order to produce virions, a packaging cell line containing the gag, pol, and env genes but without the LTR and Ψ components is constructed (Mann et al., 1983). When a recombinant plasmid containing a gene of interest, together with the retroviral LTR and Ψ sequences is introduced into this cell line (by calcium phosphate precipitation for example), the Ψ sequence allows the RNA transcript of the recombinant plasmid to be packaged into viral particles, which are then secreted into the culture media (Nicolas & Rubenstein, 1988; Temin, 1986; Mann et al., 1983). The media containing the recombinant retroviruses is then collected, optionally concentrated and used for gene transfer. Retroviral vectors are able to infect a broad variety of cell types. However, integration and stable expression require the division of host cells (Paskind et al., 1975).

An alternative approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact Ψ sequence from the recombinant virus inserts upstream from the gag, pol, env sequence integrated in the host cell genome. However, new packaging cell lines are now available that should greatly decrease the likelihood of recombination (Markowitz et al., 1988a; Hersdorffer et al., 1990).

The recombinant retroviral vectors with the hammerhead ribozymes are preferably packaged in the GP+env Am12 cell line through the retroviral packaging signal sequence (Ψ) although other cell lines may also be employed. For exemplary purposes, the viral supernatant with the ribozymes of such a vector was used to infect H226Br tumor cells. The expressed ribozyme should bind p53 pre-mRNA through its two flanking sequences complementary to intron 5 and exon 6. The normal, but not the mutant, ribozyme can cleave p53 pre-mRNA at 3' of codon 187 (GUC) because of a tertiary conformation difference between the normal and mutant ribozymes.

b. Adenovirus

Knowledge of the genetic organization of adenovirus, a 36 kB, linear and double-stranded DNA virus, allows substitution of a large piece of adenoviral DNA with foreign sequences up to 7 kB (Grunhaus & Horwitz, 1992). In contrast to retrovirus, the infection of adenoviral DNA into host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in the human.

Adenovirus is particularly suitable for use as a gene transfer vector because of its mid-sized genome, ease of manipulation, high titer, wide target-cell range, and high infectivity. Both ends of the viral genome contain 100–200 base pair (bp) inverted terminal repeats ("ITR"), which are cis elements necessary for viral DNA replication and packaging. The early (E) and late (L) regions of the genome contain different transcription units that are divided by the onset of viral DNA replication. The El region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes, including the majority of the viral capsid proteins, are expressed only after significant processing of a single primary transcript issued by the major late promoter ("MLP"). The MLP (located at 16.8 m.u.) is particularly efficient during the late phase of infection, and all the mRNAs issued from this promoter possess a 5' tripartite leader (TL) sequence which makes them preferred mRNAs for translation.

In the current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure. Use of the YAC system is an alternative approach for the production of recombinant adenovirus.

Generation and propagation of adenovirus vectors, which are replication deficient, depend on helper cell lines, such as the one designated 293 which was transformed from human embryonic kidney cells by Ad5 DNA fragments and constitutively expresses El proteins (Graham et al., 1977). Since the E3 region is dispensable from the adenovirus genome (Jones & Shenk, 1978), the adenovirus vectors, with the help of these cells, carry foreign DNA in either the El, the E3 or both regions (Graham & Prevec, 1992). In nature, adenovirus can package approximately 105% of the wild-type genome (Ghosh-Choudhury, et al., 1987), providing capacity for about 2 extra kB of DNA. Combined with the approximately 5.5 kB of DNA that is replaceable in the El and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the El deleted virus is incomplete. For example, leakage of viral gene expression has been observed with the currently available adenovirus vectors at high multiplicities of infection (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the method of the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus El region. Thus, it will be most convenient to introduce the nucleic acid encoding a ribozyme and/or p53 at the position from which the E1 coding sequences have been removed. However, the position of insertion of these coding regions within the adenovirus sequences is not critical to the present invention. The nucleic acid encoding a ribozyme and/or p53 transcription unit also may be inserted in lieu of the deleted E3 region in E3 replacement vectors, or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming unit (PFU)/ml, and they are highly infective. The life cycle of adenovirus does not require integration into the host cell genome. The foreign genes delivered by adenovirus vectors are episomal, and therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus & Horwitz, 1992; Graham & Prevec, 1992). Recently, animal studies suggested that recombinant adenovirus could be used for gene therapy (Stratford-Perricaudet & Perricaudet, 1991; Stratford-Perricaudet et al., 1990; Rich et al., 1993). Experiments in administering recombinant adenovirus to different tissues include trachea instillation (Rosenfeld et al., 1991; 1992), muscle injection (Ragot et al., 1993), peripheral intravenous injection (Herz & Gerard, 1993), and stereotactic inoculation into the brain (Le Gal La Salle et al., 1993).

c. Other Viral Vectors as Expression Constructs

Other viral vectors may be employed as expression constructs in the present invention. Vectors derived from viruses such as vaccinia virus (Ridgeway, 1988; Baichwal & Sugden, 1986; Coupar et al., 1988) adeno-associated virus (AAV) (Ridgeway, 1988; Baichwal & Sugden, 1986; Hermonat & Muzycska, 1984) and herpesviruses may be employed. They offer several attractive features for various mammalian cells (Friedmann, 1989; Ridgeway, 1988; Baichwal & Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This indicates that large portions of the genome could be replaced with foreign genetic material. The hepatotropism and persistence (integration) were particularly attractive properties for liver-directed gene transfer. Chang et al. (1991) recently introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

For applications in which the nucleic acid segments of the present invention are incorporated into vectors, such as plasmids, cosmids or viruses, these segments may be combined with other DNA sequences, such as promoters, polyadenylation signals, restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol.

DNA segments encoding a specific gene may be introduced into recombinant host cells and employed for expressing a specific RNA, such as a ribozyme or a mRNA. Alternatively, through the application of genetic engineering techniques, subportions or derivatives of selected genes may be employed. Upstream regions containing regulatory regions such as promoter regions may be isolated and subsequently employed for expression of the selected gene.

c. Therapeutic Methods

The inventors propose that the regional delivery of the expression constructs of the present invention to cancer cells in patients with p53-linked cancers, such as unresectable obstructing endobronchial cancers, will be a very efficient method for delivering a therapeutically effective gene and ribozyme to counteract the clinical disease. It is proposed that this approach is a significant improvement on current cancer therapies which rely on attempts to kill or remove the last cancer cell. Tumor cell dormancy now being an established phenomenon, effective killing of cancer cells is somewhat suspect, at least in terms of complete eradication.

Patients with unresectable endobronchial tumor recurrence that is partially or completely obstructing the airway and that have failed or are unable to receive external beam radiotherapy will be considered for this protocol. Existing therapies for this condition offer only short-term palliation. Most patients exhibit recurrences despite external beam radiotherapy. It may be possible to insert a brachytherapy catheter and administer additional radiotherapy. Patients receiving this treatment have a median survival of 6 months. Patients failing brachytherapy would also be eligible to receive gene therapy. Tumors can be removed from the airway with laser or biopsy forceps. This can be done in conjunction with injection of the expression constructs, thus decreasing the volume that must be injected. The administration of the viral constructs would not preclude the patient from receiving other palliative therapy if the tumor progresses.

1. DNA Transfer Techniques

In order to effect expression of ribozymes or p53 constructs, the expression construct must be delivered into a cell. This delivery may be accomplished in vitro, as in laboratory procedures for transforming cells lines, or in vivo or ex vivo (see below), as in the treatment of certain disease states. As described above, the preferred mechanism for delivery is via viral infection where the expression construct is encapsulated in an infectious viral particle.

Several non-viral methods for the transfer of expression constructs into cultured mammalian cells also are contemplated by the present invention. These include calcium phosphate precipitation (Graham & Van Der Eb, 1973; Chen & Okayama, 1987; Rippe et al., 1990) DEAE-dextran (Gopal, 1985), electroporation (Tur-Kaspa et al., 1986; Potter et al., 1984), direct microinjection (Harland & Weintraub, 1985), DNA-loaded liposomes (Nicolau & Sene, 1982; Fraley et al., 1979) and lipofectamine-DNA complexes, cell sonication (Fechheimer et al., 1987), gene bombardment using high velocity microprojectiles (Yang et al., 1990), polycation transfer (Boussif et al., 1995) and receptor-mediated transfection (Wu & Wu, 1987; 1988). Some of these techniques may be successfully adapted for in vivo or ex vivo use.

Once the expression construct has been delivered into the cell the nucleic acid encoding a ribozyme or wild-type p53 may be positioned and expressed at different sites. In certain embodiments, the nucleic acid encoding a ribozyme or wt-p53 may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of $CaPO_4$ precipitates into liver and spleen of adult and newborn mice demonstrating active viral replication and acute infection. Benvenisty & Neshif (1986) also demonstrated that direct intraperitoneal injection of $CaPO_4$ precipitated plasmids results in expression of the transfected genes. It is envisioned that DNA encoding a ribozyme or p53 may also be transferred in a similar manner in vivo and express a ribozyme or p53.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a ribozyme or wt-p53 may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh & Bachhawat, 1991). Also contemplated are lipofectamine-DNA complexes.

Liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacteriophage promoter is employed in the DNA construct, it also will be desirable to include within the liposome an appropriate bacteriophage polymerase.

Other expression constructs which can be employed to deliver a nucleic acid encoding a ribozyme or wt-p53 into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu & Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu & Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a 0 ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, a nucleic acid encoding a ribozyme or wt-p53 also may be specifically delivered into a cell type such as lung, epithelial or tumor cells, by any number of receptor-ligand systems with or without liposomes. For example, epidermal growth factor ("EGF") may be used as the receptor for mediated delivery of a nucleic acid encoding a ribozyme or wt-p53 in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells, in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

During in vitro culture conditions the expression construct may then deliver and express a nucleic acid encoding a ribozyme or wt-p53 into the cells. Finally, the cells may be reintroduced into the original animal, or administered into a distinct animal, in a pharmaceutically acceptable form by any of the means described below. Thus, providing an ex vivo method of treating a mammal with a pathologic condition is within the scope of the invention.

2. Pharmaceutical compositions

Pharmaceutical compositions of the present invention comprise an effective amount of the expression construct dissolved or dispersed in a pharmaceutically acceptable carrier, such as a pharmaceutically acceptable buffer, solvent or diluent, or aqueous medium. Such compositions also can be referred to as inocula.

The phrases "pharmaceutically or pharmacologically acceptable" refers to molecular entities and compositions that do not produce an adverse, allergic or other untoward reaction when administered to a human. As used herein the terms "pharmaceutically acceptable carrier" and "pharmaceutically acceptable buffer, solvent or diluent" include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalents and the like.

3. Routes of Administration

As used herein the terms "contact" "contacted", and "contacting", are used to describe the process by which an effective amount of a pharmacological agent, e.g., the expression constructs disclosed in the present invention, comes in direct juxtaposition with the target cell.

For methods of treating mammals, pharmaceutical compositions may be administered by a variety of techniques, such as parenteral, topical or oral administration.

For example, the active constructs also be formulated for parenteral administration, .e.g., formulated for injection via the intravenous, intramuscular, sub-cutaneous, or even intraperitoneal routes. The preparation of an aqueous composition that contains an expression construct agent as an active ingredient will be known to those of skill in the art in light of the present disclosure. Typically, such compositions can be prepared as injectables, either as liquid solutions or suspensions; solid forms suitable for use in preparing solutions or suspensions upon the addition of a liquid prior to injection can also be employed; and the preparations can also be emulsified.

Solutions of the active constructs as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The expression construct can also be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active constructs in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variations in dosage will necessarily occur depending on the condition of the subject being treated. The person responsible for administration will, in any event, determine the appropriate dose for the individual subject.

Even though the invention has been described with a certain degree of particularity, it is evident that many alternatives, modifications, and variations will be apparent to those skilled in the art in light of the foregoing disclosure. Accordingly, it is intended that all such alternatives, modifications and variations which fall within the spirit and the scope of the invention be embraced by the defined claims.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example I

Stable Expression of the Wild-Type p53 Gene in Human Lung Cancer Cells after Retrovirus-Mediated Gene Transfer This example demonstrates the long-term stable expression of wild-type p53 in human lung cancer cells using retroviral-mediated gene transduction. The wild-type p53 gene product has been shown to suppress features of the malignant phenotype in several human cancer cells lines (Baker et al., 1989, 1990; Nigro et al., 1989; Diller et al., 1990; Mercer et al., 1990; Michalovitz et al., 1990), but the precise mechanism of that function remains elusive. Transfection studies in vitro showed that wild-type p53 arrests growth and reduces cell proliferation. However, in these transfection studies only cells that expressed a mutant p53 protein arising by spontaneous mutation are rescued and grown as continuous cell lines (Baker et al., 1990; Takahashi et al., 1992).

A β-actin promoter, which is a strong promoter in a wide range of cell types (Gunning et al., 1987), and a retroviral vector to establish a model gene transfer system were employed in this example. The gene transfer efficiency and the effect of gene integration and expression on these lung cancer cells were investigated and it was found that expression of wild-type p53 greatly inhibited growth of the transduced human lung cancer cell lines H358a and H322a, which have deleted and mutated p53, respectively. Transduction with the retroviral construct resulted in integration and expression of the wild-type p53 gene in H358a and H322a cells that was stable for 6 months. Reduction in cell proliferation exceeded that expected on the basis of the retroviral transduction efficiency, indicating that the transduced cells can affect proliferation of nontransduced cells in the same population. A bystander effect with transduced cells reducing the proliferation rate of nontransduced cells in mixing studies was implicated. The existence of bystander effects indicates that therapeutic effects may occur in vivo without transduction of all tumor cells.

A. Materials and Methods

1. Cell Cultures

Human NSCLC cell lines H322a, H460a, and H358a were obtained from Drs. J. D. Minna and A. F. Gazdar, and were grown in RPMI medium containing 5% (H322a and H460a) or 10% (H358a) fetal calf serum (Sigma Chemical Co., St. Louis, Mo.). The clonal derivatives of the cells lines that were used in this study have been described (Putnam et al., 1992). NIH-3T3 cells and ecotropic retrovirus packaging cell line ψ2 (Mann et al., 1983) were grown in DMEM (GIBCO, Grand Island, N.Y.) with glucose (4.5 grams/liter) and supplemented with 10% fetal calf serum. The amphotropic packaging cell line, GP+env Am12 (Markowitz et al., 1988b), obtained from Dr. Arthur Bank, was grown in DMEM containing glucose, 10% newborn calf serum, HXM medium containing 15 µg/ml hypoxanthine, 250 µg/ml xanthine, and 25 µg/ml mycophenolic acid and 200 µg/ml hygromycin B (purchased from Sigma).

2. Construction of the Recombinant Retroviruses

A 2.3-kb wild-type p53 cDNA fragment with 5' and 3' untranslated sequences (Zakut-Houri et al., 1985) was subcloned into the Apr-I-neu expression vector (Gunning et al., 1987) in which p53 RNA was driven by a β-actin promoter.

A 6.6-kb fragment containing the β-actin promoter and the p53 cDNA was isolated by Eco RI/Nde I from the Apr-I-neu-p53 plasmid construct, blunt ended with Klenow enzyme, and attached in a Bgl II linker. The LNSX retroviral vector, which has been described previously (Osborne & Miller, 1988; Miller et al., 1988; Miller & Rosman, 1989) was obtained from Dr. A. D. Miller. The p53 CDNA β-actin promoter fragment was subcloned in two orientations [LNSX/p53(a)] and [LNSX/p53(b)] into the Hind III site of retroviral vector LNSX by the same methods used to attach the Bgl II linker. Expression of the neomycin-resistant gene neo, which encodes neomycin phosphotransferase, was driven by LTR (Moloney leukemia virus) promoter, while exogenous p53 expression was driven by the β-actin promoter. The 1.6-kb mutant p53 CDNA (codon 273 G→A mutation), obtained from Dr. Bert Vogelstein, was subcloned into the same retroviral vector.

3. Transfection and Infection Efficiency Assay

The amphotropic packaging cell line GP+env Am12 was transfected with the recombinant retroviral constructs or with the vector alone by the calcium phosphate method (Graham & Van Der Eb, 1973). The transfected cells were selected in HXM medium containing G418 (400 μg/ml), and clones were picked up individually 10–14 days later. The viral titer was tested by infecting NIH-3T3 cells (Miller & Rosman, 1989). The highest-titer Gp+env Am12 cells with LNSX/p53 (a) ($2 \times 10^6$) were mixed with ecotropic packaging cell line ψ2 at a ratio of 1:1. A total of $5 \times 10^5$ cells from this mixture was seeded onto 100-mm plates and passaged continuously for 1 month. These cells were then selected by HXM medium (containing 200 μg/ml hygromycin B and 400 μg/ml G418) for 10–14 days. The titer of LNSX/p53(a) was $4 \times 10^7$ cfu/ml; LNSX/p53(b) had a titer of $5 \times 10^5$ cfu/ml.

Supernatants from NIH-3T3 cells transduced by supernatants from GP+env AM12-producers cells and selected with 400 μg/ml G418 for 10–14 days (short-term assay) or passaged continuously for 1 month without G418 selection (long-term assay) were used to infect fresh NIH-3T3 cells to detect the existence of replication-competent retrovirus. Supernatants from producer cells, containing five infectious retroviral particles per milliliter, were used as a positive control.

To determine the transduction efficiency of the recombinant retrovirus, H460a, H322a, and H358a cells were transduced with LNSX/p53 (a) or LNSX by incubating $10^4$ cells with 0.5 ml of retroviral stock produced by GP+env AM12 in the presence of 8 μg/ml of Polybrene. The cells were infected daily for 1–5 days, and equal numbers of the infected H460a, H322a, and H358a cells were seeded into either a selective medium containing 300 μg/ml of G418 or a nonselective medium containing no G418 for 10–14 days. G418 titration curves showed that 300 μg/ml of G418 was cytotoxic to all lung cell lines used in this example. The infection efficiency was measured by dividing the number of G418-resistant colonies by the number of colonies in the unselected samples. The supernatant with the highest viral titer was used to infect the NSCLC cell lines. For each cell line $5 \times 10^5$ cells were seeded into 60 mm dishes. The next day, the media was replaced with 0.5 ml of retrovirus stock in the presence of 8 μg/ml of Polybrene, and, 2 hr later, 4 ml of DMEM media was added. Thus, the multiplicity of infection ("moi") ranged from 40:1 to 1:1, depending on the construct. G418 selection (300 μg/ml) was begun 48 hr later. After 15 days, rescued clones were pooled and maintained in selective media.

4. Northern Blot Analysis

Total cellular RNA was isolated using guanidine isothiocyanate (Chomczymsky & Sacchi, 1987). The RNA (10 μg per lane) was denatured with 6% formaldehyde and 50% formamide, size-fractionated on a 1.5% agarose gel containing 6% formaldehyde, and blotted on to a GeneScreen™ membrane. The membrane was hybridized with the p53 cDNA BamHI fragment probe: prehybridization, hybridization, and posthybridization washes were done essentially as described in GeneScreen™ protocols.

5. Western Blot Analysis

Total cellular protein was extracted from control and transduced cell lines. Subconfluent cells were rinsed with cold phosphate-buffered saline ("PBS") three times and lysed in buffer containing 2% sodium dodecyl sulfate ("SDS") and 10% glycerol in 50 mM Tris-HCl pH 6.8. Cell lysates were heated at 100° C. for 5 min, followed by centrifugation for 10 min. The protein concentration of the supernatant was determined spectrophotometrically by the BCA protein assay system. All cell extracts were adjusted to contain 5% β-mercaptoethanol. Fifty micrograms of protein was size-fractionated in 10% polyacrylamide gel and electroblotted onto a nitrocellulose membrane. The primary antibody against p53, PAb 1801 (Oncogene Science, Manhasset, NY) and horseradish peroxidase-conjugated rabbit anti-mouse immunoglobulin G (Pierce) were used to detect p53 protein in the cell lines according to the protocol outlined for the Amersham ECL Chemiluminescent Western System (Amersham, Arlington Heights, Ill.).

6. Immunohistochemistry

Transduced cells were grown on chamber slides (Nunc, Naperville, Ill.). Following fixation with 3.8% formalin, the slides were treated with 3% $H_2O_2$ in methanol for 5 min. Slides were stained with the anti-p53 antibody PAb 1801 by the avidin-biotin method (Vectastain Elite kit, Vector, Burlingame, Calif.).

7. PCR Analysis of Genomic DNA from Transduced Cells

PCR was performed as previously described (Saiki et al., 1985). Two neomycin Phosphotransferase oligonucleotide primers, neo 1 (5'-CAAGATGGATTGCACGCAGG-3') (SEQ ID NO:1) and neo 5 (5'-CCCGCTCAGAAGAACTCGTC-3') (SEQ ID NO:2) were synthesized. Conditions for amplification of a 790-bp fragment of the neo gene were incubation at 94° C. for 1 min, 50° C. for 1 min, 72° C. for 2 min, and in the last cycle, 72° C. for 10 min, through 35 cycles. The amplified PCR products were electrophoresed, transferred onto a Gene-Screen™ membrane, and hybridized with $^{32}$P-labeled nick-translated neo gene probe (a neo gene fragment isolated by Hind III/Sma I from psv2-neo plasmid DNA).

8. RNA-PCR Analysis and Slot Oligonucleotide Hybridization

Total cellular RNA was isolated from control and transduced cell lines, and cDNA was synthesized in a total volume of 20 μl containing 5 μg of RNA, 150 units of reverse transcriptase from avian myeloblastosis virus (Boehringer Mannheim Biochemica), and oligo(dT) as a primer (Gunning et al., 1987). The region of the p53 RNA corresponding to exon 7 was amplified by PCR from the CDNA using primers 5'-TCTGACTGTACCACCATCCT-3' (SEQ ID NO:3) and 5'-CTGGAGTCTTCCAGTGTGAT-3' (SEQ ID NO:4). Denaturation, annealing, and extension were done at 92° C. for 1 min, 58° C. for 1 min, and 72° C. for 1 min, and in the last cycle, 72° C. for 10 min, through 35 cycles. The resulting 104-bp PCR-amplified fragment was blotted onto a Gene Screen membrane by a slot-blot apparatus (Schleicher & Schuell, Keene, N.H.). Two oligonucleotide probes, a wild-type sequence, 5'-GATGGGCCTCCGGTTCATGCC-3' (SEQ ID NO:5), and a mutated sequence, 5'-GATGGGCCTCAGGTTCATGCC-3' (SEQ ID NO:6), were used to detect expression of the wild-type and mutated p53 genes. The filters were prehybridized and hybridized at 56° C. in 3 M EDTA, 0.1% SDS, 5×Denhardt's solution, and 100 μg/ml of salmon sperm DNA for 2 hr. The filters were washed twice in a 2×solution of sodium chloride, SDS, phosphate buffer and EDTA ("SSPE"), 0.1SDS solution at room temperature, and once for 20 min at 58 C. in a 5×SSPE, 0.1% SDS solution. The filters were washed for 15 min at 68° C. The filters were exposed to X-ray film for 1–3 days at −80° C. The Exxon 7A amplimer was used to reprobe the filters to confirm that the samples had been equally loaded.

B. Results

Figure 5:
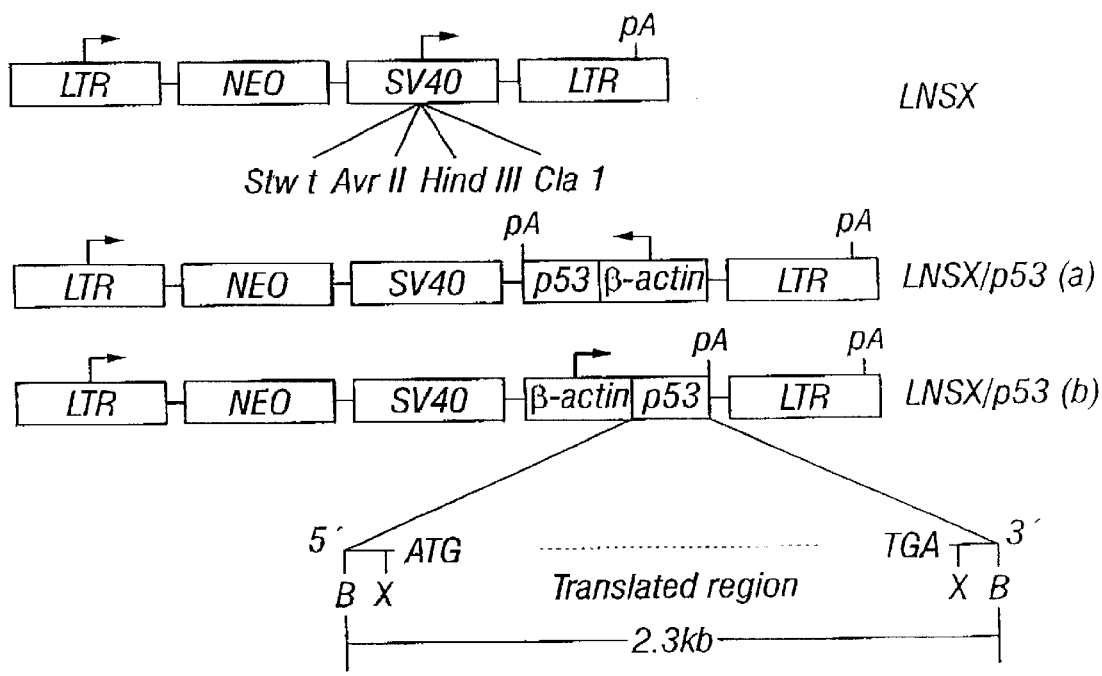
FIG. 5. Plasmid maps of the retroviral expression vectors. A 6.6-kb fragment containing p53 CDNA with 5' and 3' untranslated region and a β-actin promoter was subcloned into the Hind III site of retrovirus vector LNSX in two orientations. Arrows indicate direction of LTR and β-actin promoters transcription; pA, polyadenylation signals; B, Bam HI; X, Xba I.

A 6.6-kB fragment containing p53 CDNA and a β-actin promoter was subcloned into retroviral vector LNSX in two orientations. In orientation (a), the β-actin promoter was 3' to the p53 CDNA and the direction of p53 transcription was opposite to that of the 5' retroviral LTR. In orientation (b), the β-actin-p53 cassette was reversed, and the direction of p53 transcription was the same as the 5' retroviral LTR (FIG. 5).

To increase the titer of the recombinant retrovirus, amphotropic GP+env AM12 cells transfected by LNSX/p53(a) were co-cultured with ecotropic packaging cell line ψ2 for 1 month. Individual colonies were selected in HXM medium with hygromycin B and G418. The highest viral titer generated by testing the selected colonies was 4×10$^7$ cfu as determined by transduction and selection of NIH-3T3 cells.

The presence of replication-competent virus was measured by infection of fresh NIH-3T3 cells with medium conditioned in NIH-3T3 cell cultures infected by recombinant retrovirus and selected by G418 for 10–14 days (short-term assay). In a more sensitive long-term assay, NIH-3T3 cells were infected with the medium conditioned by GP+env Am12 producing cells, after which they were passaged for 1 month to allow for the spread and amplification of rare recombinant wild-type virus in the culture. Medium collected from these NIH-3T3 cells was used to infect fresh NIH-3T3 cells. Both the short-term and long-term assays showed that no detectable replication-competent retrovirus was produced by Gp+env Am12 cells.

The expression of p53 cDNA by the two constructs was compared. Both retroviral vectors successfully integrated a neo gene fragment into transduced H358a and H322a cells. In a Northern blot analysis with p53 CDNA as a probe, only one p53 band similar to the endogenous p53 mRNA fragment was observed in H358a-LNSX/p53(a) 18-hr after transduction. No p53 mRNA was found in H358a-LNSX/p53(b) in a similar study. Moreover, western blot analysis showed a detectable wild-type p53 protein in H358a-LNSX/p53(a) 4 weeks following transduction. Levels of p53 protein in the positive control H322a cell line are higher because of the longer half-life of the mutant protein.

The recombinant retroviral vector LNSX/p53(b) in transduced H358a cells produced p53 mRNA of the same size as that shown by LNSX/p53(a) 6 months following transduction. However, the LNSX/p53(a) construct produced higher levels of p53 RNA than did the LNSX/p53(b) construct. Levels of p53 protein in the transduced cell lines were similar to those occurring in cells that express wild-type p53.

Expression of the wild-type p53 gene in transduced H322a cells were demonstrated by RNA-PCR analysis. A cDNA fragment was synthesized from total RNA following amplification of 104 base of exon 7 by two specific amplifiers. Two oligonucleotide probes composed of complementary corresponding sequences of exon 7 for wild-type and mutated p53 were synthesized. PCR products for exon 7 of p53 mRNA were hybridized separately with the two oligonucleotide probes. Expression of wild-type exon 7 was detected in H460a cells(al) and LNSX/p53(a)-transduced H322a cells by a $^{32}$P-end labeled wild-type oligonucleotide probe. Nontransduced H322a cells did not express wild-type p53. However, a reduction in expression of mutant exon 7 was shown when the mutant probe was used in H322a cells transduced with LNSX/p53(a) or LNSX/p53(b).

The transduction efficiency of exogenous p53 was measured by infecting H460a, H322a, and H358a cells with the high virus titer construct [LNSX/p53(a)] and selecting colonies with G418. The number of colonies after selection was compared to the number formed without selection. The LNSX retroviral vector served as an additional control. The efficiency of transduction increased with an increasing number of exposures to the retroviral vector.

Figure 6A:
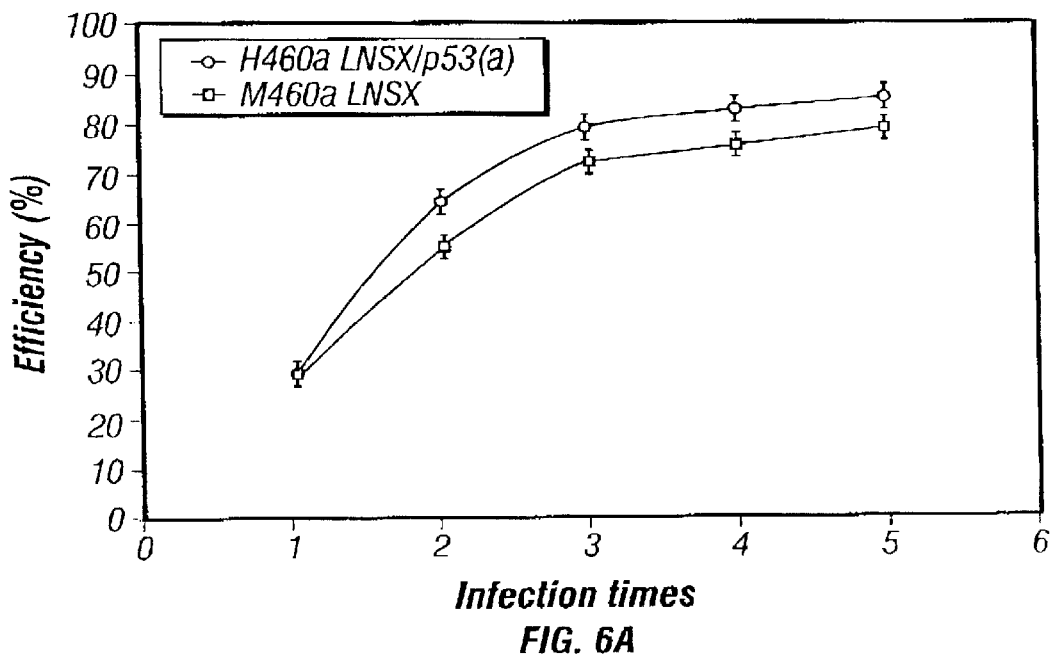
FIG. 6A, FIG. 6B, FIG. 6C, FIG. 6D, FIG. 6E, FIG. 6F. H460a, H322a or H358 cells (10⁴) were infected for 1 day or several days with 0.5 ml of viral stock and 8 µg/ml of Polybrene (every day medium was changed and replenished with fresh viral stock). After infection, cells were plated in equal numbers into selective medium containing 300 µg/ml G418 or nonselective medium. After 10 days, cells were counted to determine the transduction efficiency.

After five exposures, the transduction efficiencies were 90±5.6% in H460a cells, 93±3.7% in H322a and 88±5.2% in H358a cells. A representative example showing the transduction efficiency for H460a cells is shown in FIG. 6A. There was no significant difference between the infection efficiencies of the retrovirus LNSX alone and that of the recombinant retrovirus LNSX/p53(a).

Figure 6B:
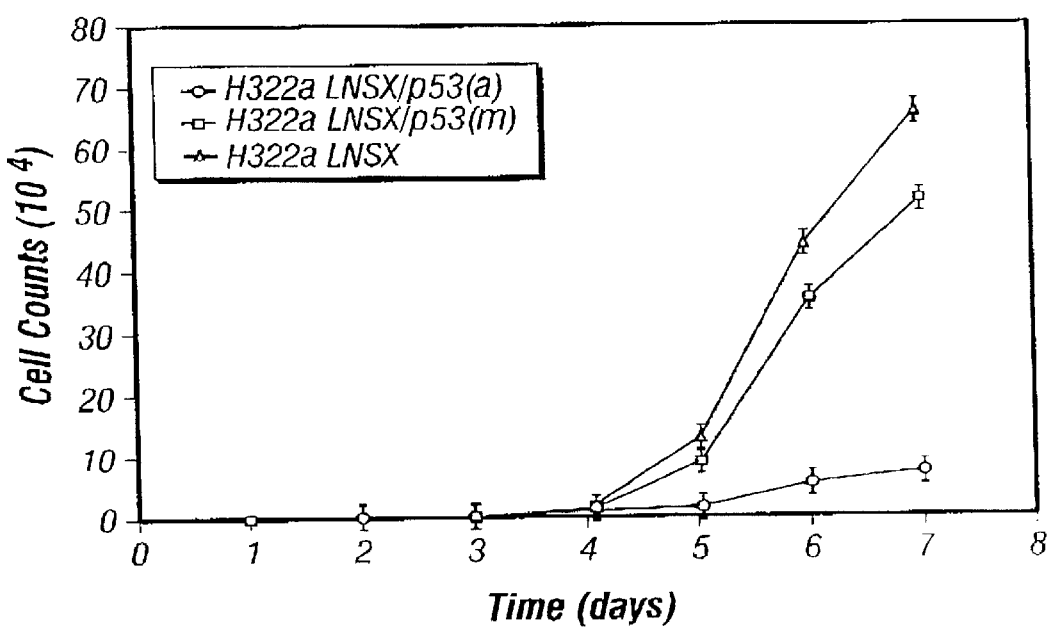
Figure 6C:
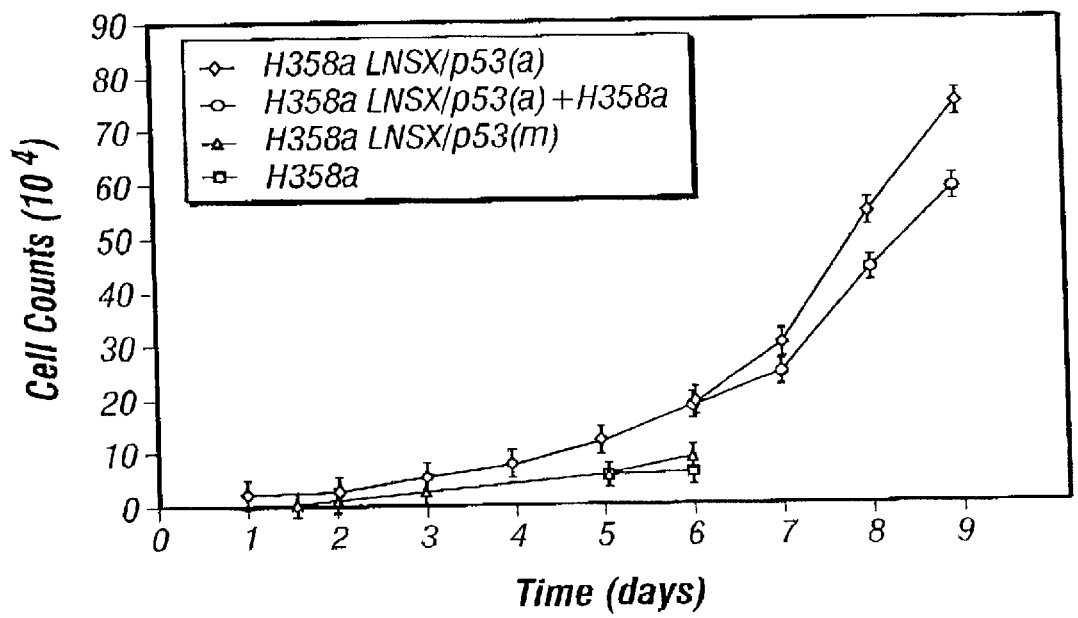
Figure 6D:
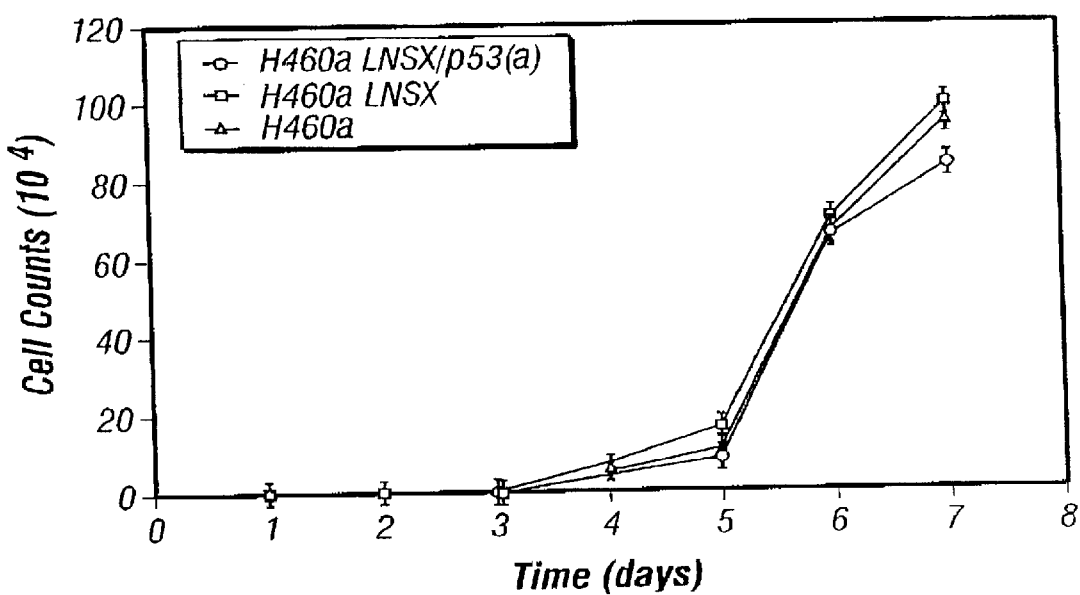

The three NSCLC cell lines studied here, H460a, H322a, and H358a, were transduced with supernate from the recombinant retrovirus or control vector to study the growth kinetics of the infected cells. It was found that introduction of wild-type p53 into cell lines H322a and H358a greatly suppressed the growth rate of these tumor cells (FIG. 6B and FIG. 6C), whereas transduction of H460a cells by LNSX/p53(a) did not suppress their growth (FIG. 6D). Growth studies were initially done in the absence of G418 selection to avoid possible effects of G418 on cell growth. The growth rate of H322a cells exposed to retrovirus two times was inhibited by 80% (FIG. 6B) and that of cells exposed once was inhibited by 60% in the absence of G418 selection. Transduction of a retroviral construct containing a mutant p53 cDNA had no effect on the growth of H358a cells (FIG. 6C). Expression of p53 protein by H358a cells transduced with the mutant p53 construct was shown by immunohistochemistry with the PAb 1801 anti-p53 antibody.

Figure 6E:
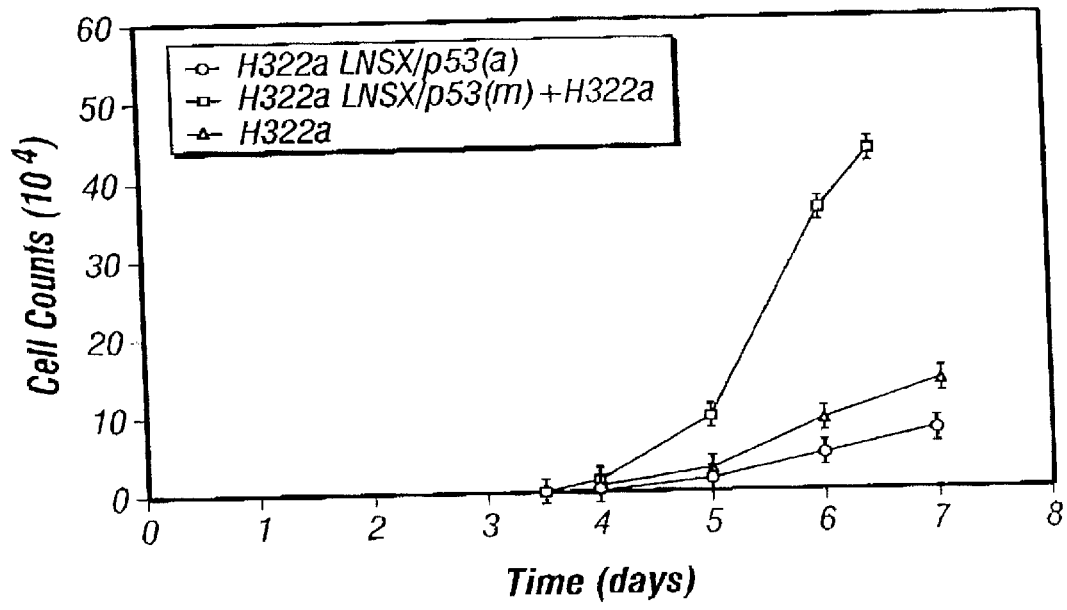
Figure 6F:
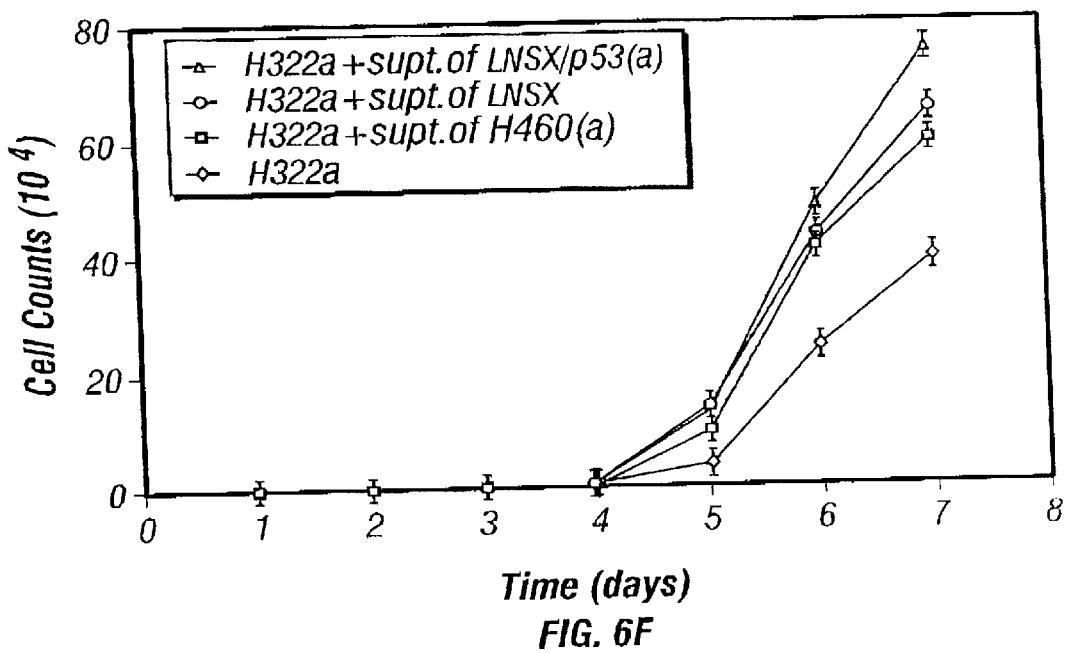

Transduction efficiency of cells exposed to the LNSX/p53(a) construct was 30% after one exposure and 50% after two exposures. This compares with the observation of a 60% reduction in cell number after one exposure and 80% after two exposures in an unselected population (FIG. 6B). This suggested that the transduced cells may alter the growth of the nontransduced population. To test this, transduced and G418 selected H358a and H322a LNSZ/p53(a) cells and nontransduced cells were mixed at a ratio of 1:1 (FIG. 6C and FIG. 6E). The growth curves for the mixed population were not significantly different from that of a G418-selected population of transduced cells. Analysis of the proportion of transduced cells in the mixed population showed that 44±5% of the cells in the mixed culture were transduced at day 9 following G418 selection. The fixed proportion of transduced cells in the day 9 culture was consistent with the hypothetical growth-inhibitory influence of transduced on nontransduced cells. Supernate from H322a cells transduced with LNSX/p53(a) suppressed the growth of H322a cells, whereas supernate from LNSX-transduced H322a cells and supernate from H460a cells, which have a wild-type p53, had no effect, suggesting that a factor or factors produced by the transduced cells may mediate this effect (FIG. 6F).

c. Discussion

Retrovirus-mediated introduction of the wild-type p53 gene into NSCLC cell lines greatly suppressed the growth rate of H358a and H322a cells. The growth of H460a cells, which have an endogenous wild-type p53 gene, was not altered. Expression of wild-type p53, which was examined separately at 18 hr, 1 month, and more than 6 months after infection, indicates that a stable, intact restoration of the wild-type p53 gene was achieved. This stable expression of wild-type p53 in transduced cell lines provides a good model of the function of the wild-type p53 gene in human cancer cells.

In the recombinant retroviral vectors, the orientation (a) vector showed higher levels of p53 expression. It is contemplated that other retroviral promoters in the construct will suppress the β-actin promoter, as described in other systems, when all promoters are aligned in the same direction of transcription (Emerman & Temin, 1984). Another possible explanation is that the intron and its enhancer in the β-actin promoter are spliced out of the retroviral message during the first round of retroviral replication in orientation (b). However, other retroviral promoters are not as active as the β-actin promoter, and therefore this effect may have some degree of promoter specificity (Emerman & Temin, 1984; Gunning et al., 1987). If some antisense transcripts were produced in orientation (a), alternate transcripts should have been detected by Northern analysis. However, these transcripts were not detected. The effectiveness in expression of functional p53 protein by the orientation (a) construct supports the absence of inhibition by antisense. The use of β-actin promoter in orientation (b) with an LNL6 retrovirus yielded low rates of infectivity and low levels of gene expression (Owens & Boyd, 1991). Therefore, to maximize expression of p53, it may be advantageous to utilize different transcriptional orientations for the genes inserted in the retroviral vector.

Previous studies of transfection with plasmid expression vectors showed that the presence of the wild-type p53 gene can suppress growth of various human tumor cell lines (Baker et al., 1990; Mercer et al., i990; Takahashi et al., 1992). This is not due to a general toxic effect but is reversible (Michalovitz et al., 1990). However, in most studies the clones rescued contained an altered p53 gene. Suzuki et al. (1992) transfected a wt-p53 plasmid into NSCLC NCI-H23 cells and isolated a clone expressing wt-p53. This clone lost tumorigenicity in severe combined immunodeficiency ("SCID") mice. In a previous study using a retroviral vector to transduce p53 into osteosarcoma cells, some stable clones expressing wild-type p53 were isolated (Chen et al., 1990). The efficiency of transduction and the long-term stability of these clones were not noted. Expression of p53 protein was comparable to that seen in the instant example. The high efficiency of retroviral transduction achieved by the present invention permits development of multiple tumor cells lines stably expressing p53.

The influence of transduced cells expressing wild-type p53 on nontransduced cells is interesting and unexpected. This effect was also found in rat glioma cells infected by exogenous Herpes simplex thymidine kinase (HS-tK). When the thymidine kinase-transduced cells were mixed with parental cells at a ratio of 1:10, tumorigenesis in mice was greatly suppressed when transduced cells were exposed to the antiviral drug ganciclovir (Culver et al., 1992). The mechanism of this effect is not known, but it may be mediated by toxic metabolites of the ganciclovir. The effect seen with p53-transduced cells was not as great but was highly reproducible when mixtures contained at least 50% transduced cells. The growth rates of nonselected transduced cultures, measurement of the remaining fraction of transduced cells following mixing studies, and inhibition by supernates specifically from p53 transduced cells all supported the existence of this effect.

EXAMPLE II

Therapeutic Effect of a Retroviral Wild-Type p53 Expression Vector in an Orthotopic Lung Cancer Model Mutations of the p53 tumor suppressor gene (also known as Tp53) are the genetic abnormalities most frequently identified in NSCLC (Takahashi et al., 1989). The wild-type form of p53 usually is dominant over the mutant. It is known that restoration of the wild-type p53 gene by a retroviral vector suppresses the growth of NSCLC cell lines in vitro and induces apoptosis in multicellular NSCLC tumor spheroids (Cai et al., 1993; Fujiwara et al., 1993).

This example discloses the therapeutic efficacy of intratracheal inoculation of the wild-type p53 retroviral supernatant in suppressing human NSCLC tumor formation in an orthotopic mouse model. Infection with LNp53B inhibited proliferation of H226Br cells in vitro. Thirty days after tumor cell inoculation, 62%–80% of the control mice showed macroscopic tumors of the right main stem bronchus. LNp53B suppressed H226Br tumor formation in 62%–100% of mice, and the effect was abrogated by dilution of the retroviral supernatant with inactive vector. Direct administration of a retroviral vector expressing wt-p53 may inhibit local growth in vivo of human lung cancer cells with abnormal p53 expression.

A. Materials and Methods

1. Cells and Culture Conditions

The inventors routinely propagated the following two human NSCLC cell lines in monolayer culture in RPMI-1640 medium with 10% fetal calf serum (Sigma Chemical Co., St. Louis, Mo.): 1) H226Br, whose p53 gene has a homozygous mutation (mut-p53) at codon 254; and 2) H358a, a clonal derivative of H358, whose p53 gene is homozygously deleted. The H226Br cell line is a variant of the H226 cell line derived from a brain metastasis in a nu/nu mouse (obtained from I. J. Fidler, The University of Texas M.D. Anderson Cancer Center, Houston). The H358 and H226 cell lines were obtained from A. Gazdar (Simmons Cancer Center, Dallas, Tex.) and J. Minna (Simmons Cancer Center) and have been previously described (Mitsudomi et al., 1992). The amphotropic packaging cell line GP+env Am12 and the ecotropic packaging cell line GP+E-86 (Markowitz et al., 1988b) were grown in Dulbecco's modified Eagle medium (GIBCO BRL, Grand Island, N.Y.) with a high glucose concentration (4.5 g/L) supplemented with 10% newborn calf serum. For selecting GP+env AM12 cells, the inventors used HXM medium containing hypoxanthine (15 $\mu$g/mL), xanthine (250 $\mu$g/mL), mycophenolic acid (25 $\mu$g/mL), and hygromycin B (100 $\mu$g/mL).

2. Construction and Generation of a Replication-defective Retroviral wt-p53 Expression Vector A 1.8-kilobase (kb) wt-p53 complementary DNA (CDNA) fragment linked to a β-actin promoter was subcloned into the LNSX retroviral vector (Miller & Rosman, 1989) at 3' to 5' orientation following removal of a SV40 promoter contained in the original LNSX vector (Cai et al., 1993). This vector is designated LNp53B. As a control, mut-p53 cDNA (codon 273 CGT to CAT), obtained from B. Vogelstein (The Johns Hopkins University Medical School, Baltimore, Md.), was also cloned into the same retroviral vector. The GP+env Am12 cell line was transfected with the recombinant retroviral construct by the calcium phosphate coprecipitation method (Graham & Van Der Eb, 1973). The highest titer virus-producing clone was selected in medium containing the G418 antibiotic (400 µg/ml) and was then co-cultured with the GP+E-86 cell line to further increase the viral titer. Following several passages over a period of 1 month, GP+env Am12 cells were selected in HXM medium, and the viral titer of the supernatant was tested by infecting NIH-3T3 cells. The titer of the retroviral supernatant was $8 \times 10^6$ colony-forming units (CFU)/mL. The supernatant was free of replication-competent virus, as assessed by an NIH 3T3 amplification assay capable of detecting five infectious viral particles per milliliter.

3. Cellular RNA Extraction, Polymerase Chain Reaction, and Southern Blot Analysis to Determine Messenger RNA Expression Total cellular RNA was isolated from monolayer cultures of virus-infected H226Br cells according to a previously described method (Chomczynsky & Sacchi, 1987). Briefly, cells were mixed with an equal volume of GTC solution (8 M guanidinium thiocyanate, 1% sarcosyl, and 0.05 M sodium citrate). The mixture was extracted with acid phenol-chloroform-isoamyl alcohol, and the aqueous phase was collected. RNA was precipitated with one volume of isopropanol. RNA was resuspended in 0.3 M sodium acetate and precipitated with two volumes of ethanol. Finally, the RNA pellet was resuspended in water treated with diethylpyrocarbonate. For cDNA synthesis, RNA samples were treated with 5 U ribonuclease-free deoxyribonuclease (Boehringer Mannheim Corp., Indianapolis, Ind.) for 1 hour at 37° C. in 0.1 M sodium acetate and 5 mM $MgSO_4$. The reaction was stopped by the addition of 10 mM EDTA and 0.2% SDS. Samples were phenol extracted, precipitated with ethanol, and used as a template for CDNA synthesis from messenger RNA present in the samples.

The CDNA synthesis was done in a 20-µL reaction mixture containing 40 U RNasin (Promega Corp., Madison, Wis.), 50 mM Tris-HCl (pH 8.3), 75 mM KCl, 10 mM dithiothreitol, 3 mM $MgCl_2$, 0.1 µg oligo $(dT)_{12-18}$, 0.1 mg/mL bovine serum albumin (BSA), 0.5 mM of each deoxynucleoside 5'-triphosphate ("dNTP"), and 200 U of Moloney murine leukemia virus reverse transcriptase (GIBCO BRL). The reaction mixture was incubated at 37° C. for 1 hour, and the enzyme was inactivated at 97° C. for 5 minutes and quickly chilled on ice. PCR was performed in a 50-µL reaction volume containing 20 µL of the reverse-transcribed samples, 0.1 mg/mL BSA, 50 mM KCl, 10 mM Tris-HCl (pH 9.0), 1.5 mM $MgCl_2$, 0.01% gelatin (wt/vol), 0.1% Triton X-100, 0.2 mM of each dNTP, 50 pmol of each of the 5' and 3' primers, and 1 U of Taq DNA polymerase (Promega Corp.) The amplification reaction involved denaturation at 94° C. for 1 minute, annealing at 58° C. for 1 minute, and extension at 72° C. for 1 minute using a Perkin-Elmer thermal cycler (Perkin-Elmer Corp., Mountain View, Calif.) for 35 cycles. An additional cycle for 10 minutes at 72° C. was used for complete extension. PCR products were resolved in 2% agarose TBE (1×Tris-borate-EDTA buffer) gel and transferred onto a GeneScreen™ membrane (DuPont/NEN, Boston, Mass.) for Southern blot hybridization.

4. Cellular DNA Extraction, PCR Amplification, and Southern Blot Analysis to Determine the Presence of p53 Gene Fresh tumors were washed three times with phosphate-buffered saline and were then frozen in liquid nitrogen. High-molecular-weight DNA was extracted from frozen H226Br tumors by using Gene Releaser (BioVentures, Inc., Murfreesboro, Tenn.). One microgram of DNA was used to amplify the target gene by PCR. The specific primers used for p53 were exon 7 ['5-TCTGACTGTACCACCATCCA-3' (SEQ ID NO:7) and 5'-CTGGAGTCTTCCAGTGTGAT-3' (SEQ ID NO:4)] and the promoter/p53 region of LNp53B [β-actin promoter: 5'-ACCTGCAGCCCAAGCTTCGAG-3' (SEQ ID NO:8); p53 exon 4:5'-TGCAAGTCACAGACTTGGCTG-3' (SEQ ID NO:9)]. The PCR products were resolved on a 4% agarose gel and visualized by ethidium bromide fluorescence. For Southern blotting, the PCR products were transferred onto a GeneScreen™ membrane and hybridized with a $^{32}P$-labeled, nick-translated p53 cDNA Bam H1 fragment probe.

5. Western Blot Analysis

Total cellular protein was extracted from H358a cells infected with the LNp53B. The protein was fractionated in 10% polyacrylamide gel and electroblotted onto a nitrocellulose membrane. The membrane was incubated with a primary antibody against p53, PAb 1801 (Oncogene Science, Manhasset, N.Y.), and then with the horseradish peroxidase-conjugated rabbit anti-mouse immunoglobulin G. The ECL Chemiluminescent Western System (Amersham, Arlington Heights, Ill.) was used to detect secondary probes. Anti-actin antibody was used as a control for protein loading.

6. Therapy Protocol

Eighty-four 4- to 6-week old female BALB/c nu/nu mice weighing approximately 20 g each were used. The mice were provided food (Tex Lab Sterilizable Lab Blocks; Alief Feed Co., Houston, Tex.) and water ad libitum. The mice were maintained under pathogen-free conditions. All studies involving mice were performed under protocols and guidelines approved by the M.D. Anderson Animal Care and Use Committee.

Irradiated (350 cGy) nu/nu mice were anesthetized with methoxyflurane and inoculated intratracheally with $2 \times 10^6$ H226Br cells in 0.1 mL Hanks' balanced salt solution into the right main stem bronchus via a tracheotomy. The cervical trachea was exposed by dissection of the peritracheal muscle sheath. A tracheotomy was made by puncture with a 25-gauge needle. Gentle traction on the proximal trachea with a forceps straightened the right bronchus and allowed introduction of a 27-gauge needle, which was advanced to the level of the right upper lobe orifice. The cell suspension was injected with a 1-mL syringe. Beginning 3 days after tumor cell inoculation, 0.1 mL of retroviral supernatant, mixed with 5 µg/mL protamine to enhance gene transduction (Cornetta & Anderson, 1989), was injected once daily for 3 days through the previous tracheotomy incision using a 1-mL syringe with a 27-gauge needed. The mediastinal blocks were harvested 30 days later and assessed for tumor formation and growth by the same observer, who had no knowledge of the treatment groups. The tumor volume was calculated by measuring the perpendicular diameters with linear calipers as described previously (Georges et al., 1993).

7. Statistical Analysis

Differences in the tumor volumes for the treatment groups were compared using the Wilcoxon test. Differences in the distribution of tumor incidence among study groups were determined using Fisher's exact test.

B. Results

1. Expression of wt-p53 Messenger RNA in H226Br Cells and p53 Protein Production in H358a Cells H226Br cells were transduced in vitro with the LNp53B retroviral vector by incubating $10^4$ to $10^6$ cells with 0.5 mL of retroviral stock in the presence of 8 µg/mL polybrene. This transinfection was repeated once daily for 3 days. To examine whether the transduced p53 gene was expressed in these cells; the reverse transcription-PCR analysis used sense primers for β-actin promoter sequences 5' to the promoter/p53 junctional sequences and an opposing p53 cDNA antisense primer located within p53 cDNA antisense primer located within p53 exon 4. These primers are specific for the retrovirally transduced p53. PCR products were evaluated by Southern blot hybridization with a $^{32}$p-labeled, nick-translated p53 cDNA probe. A β-actin/p53 segment was detected in H226Br cells transduced with wt-p53, whereas it was not present in parental and LNSX virus-infected cells. Western blot analysis demonstrated detectable levels of p53 protein following LNp53B retroviral infection in p53-negative H358a cells.

2. Inhibition of H226Br Cell Growth in Vitro After wt-p53 Transduction

Monolayer cultures of H226Br cells were exposed to LNp53B retrovirus, and the growth kinetics of the mass culture was assessed to examine the effect of in vitro transduction of wt-p53 on the growth of lung cancer cells. Infection by LNSX virus had no effect on the growth of H226Br cells, but LNp53B-infected cells showed a fourfold reduction in growth compared with parental cells.

3. Effect of Intratracheal Instillation of wt-p53 Retrovirus in an Orthotopic Lung Cancer Model The intrapulmonary model for the orthotopic propagation of human lung tumor cells was used to assess the effect of direct in vivo injection of the LNp53B retrovirus. H226Br tumors were successfully grown in irradiated nu/nu mice by the intratracheal inoculation of $2\times10^6$ tumor cells. Endobronchial tumors with local mediastinal extension were observed in approximately 75% of the animals 30 days after the intratracheal inoculation (Table 4). In the therapy protocol, irradiated (350 cGy) nu/nu mice were inoculated intratracheally with H226Br cells and were then inoculated intratracheally on days 4, 5, and 6 with medium only, unmodified LNSX virus, LNp53B retrovirus, or mut-p53 retrovirus. At autopsy, 30 days after tumor inoculation, only 0%–38% of mice treated with wt-p53 retroviral supernatant had right-sided lung tumors, and these tumors were much smaller than tumors in the control groups; the effect of injecting the mut-p53 virus on in vivo tumor growth, however, was not significantly different from that in control mice (Table 4). Moreover, serial dilution of LNp53B retroviral supernatant with unmodified LNSX viral supernatant reduced the efficacy of the LNp53B virus in suppressing tumor growth (Table 1). The decreasing incidence of tumors with increasing LNp53B concentrations was statistically significant (P<0.1 by Fisher's exact test).

TABLE 4

EFFECT OF wt-p53 RETROVIRAL CONSTRUCT ON ON GROWTH OF H226Br TUMOR IN NU/NU MICE

| Experiment No. | Treatment* | No. of mice with tumor/ total No. of mice treated | Mean volume ± SEM, mm$^3$† |
|---|---|---|---|
| 1 | Medium | 7/10 (70) | 2.85 ± 0.99 |
|   | LNp53B | 0/8 (0) | 0‡ |
| 2 | Medium | 7/9 (78) | 2.23 ± 0.76 |
|   | LNSX only | 5/7 (71) | 4.47 ± 1.38 |
|   | LNp53B | 3/8 (38) | 0.81 ± 0.63‡ |
|   | mut-p53 | 5/8 (62) | 3.78 ± 1.14 |
| 3 | LNSX only | 8/10 (80) | 1.43 ± 0.81 |
|   | LNSX/LNp53B (3:1) | 4/6 (67) | 1.55 ± 1.01 |
|   |  |  | 2.26 ± 0.89 |
|   | LNSX/LNp53B (1:1) | 3/8 (38) | 0.33‡ |
|   | LNp53B | 1/10 (10) |  |

*Irradiated (350 cGY) nu/nu mice were inoculated intratracheally in the right main stem bronchus with $2 \times 10^6$ H226Br cells. On days 4, 5, and 6, mice were treated with intratracheal inoculation (0.1 mL) of either medium or LNSX, LNp53B, or mut-p53 retroviral supernatants. In experiment No. 3, mixed solutions of LNSX and LNp53B viral supernatants at the indicated ratios were injected. The mediastinal blocks were harvested 30 days later, and tumor growth was evaluated.
†Mean volume is calculated only for the tumors detected.
‡P < .05 compared to control groups by the Wilcoxon test.
§P < .01 for distribution of tumor incidence by Fisher's exact test.

The one small tumor that grew in experiment No. 3 (Table 4) following treatment with LNp53B retroviral supernatant was analyzed for the presence of the retroviral p53 DNA by specific PCR. PCR primers that spanned exon 4 of p53 and the β-actin promoter recognize only exogenous p53. The exogenous sequence was detected by PCR and confirmed by Southern blot hybridization with p53 CDNA in the tumor that grew following treatment with the LNp53B retroviral vector. Only endogenous p53 was detected in DNA extracted from a tumor treated with the control LNSX vector.

C. Discussion

This example demonstrates the efficacy of retroviral vector-mediated transfer of the wt-p53 gene into human lung cancer cells in vitro and in vivo. Expression of wt-p53 inhibited the growth of H226Br cells, which have an endogenous mutant p53, suggesting that the introduction of wt-p53 may be an effective strategy to slow the growth and potentially reverse the malignant phenotype of lung cancer cells with inactive p53.

For optimal growth and progression of tumors arising from human cancer cells in vivo, organ-specific tumor implantation is critical. Intratracheal injection of human lung tumor cells into nu/nu mice induces a pattern of tumor growth similar to that observed in human lung cancer patients. In the present Example, H226Br cells were successfully grown in the pulmonary environment and formed endobronchial tumors. It was observed that the orthotopic growth of 4-day established H226Br tumors was significantly inhibited by the intratracheal administration of LNp53B retroviral supernatant in a dose-dependent fashion. A few small tumors were observed in mice treated with the LNp53B retrovirus. It is possible that some tumor cells escaped retroviral infection and formed tumors that were small because there were few residual cells. Alternatively, some tumor cells that were infected with the wt-ps3 virus continued to grow more slowly than the uninfected calls and thus formed small tumors. The detection of the p53 DNA sequence in the resultant tumor favors the latter explanation. Transduction of wild-type p53 by a retroviral vector can mediate apoptosis in some cell types but may also become stably integrated in cells, which then have a reduced rate of proliferation (Cai et al., 1993; Fujiwara et al., 1993). Variations in the site of proviral integration and the level of wild-type p53 expression are expected to influence the outcome of its effect on the cell.

Although the use of a retroviral vector favors integration in rapidly dividing tumor cells, it is unlikely that all or even most tumor cells take up the virus. This indicates that a bystander effect is operative with LNp53B-transduced H226Br cells inhibiting the growth of nontransduced H226Br cells. A bystander effect for wild-type p53-transduced lung cancer cells in culture has been previously demonstrated in studies mixing wild-type p53-transduced and nontransduced cells (Cai et al., 1993). The molecular basis of this bystander effect is currently unknown.

It has been previously reported (Georges et al., 1993) that intratracheal instillation of antisense K-ras retroviral supernatant prevented the orthotopic growth of human H460a lung cancer cells, which have a codon 61 mutation of the K-ras oncogene. In another study (Fujiwara et al., 1993), in situ PCR hybridization indicated that the wt-p53 retroviral vector is capable of multilayer penetration into the three-dimensional structure of multicellular tumor spheroids. Taken together, these results indicate that microscopic tumors established in the bronchial epithelium are efficiently infected with a retroviral vector expressing therapeutic genes and that in situ retrovirus-mediated gene transfer provides a useful strategy for manipulating genetic abnormalities of cancer calls in vivo. Recent progress in the methodology of molecular genetics has made it possible to identify genetic lesions, such as the inactivation of tumor suppressor genes by mutations or deletions in premalignant lesions (Casson et al., 1991). Specific gene-replacement approaches based on the type of mutation found in the target cancer will useful as an adjunct to conventional therapies that improve the prognosis of NSCLC patients and the development of gene-specific prevention strategies.

EXAMPLE III

Suppression of Lung Cancer Cell Growth by Ribozyme-Mediated Modification of P53 Pre-mRNA This example teaches that a ribozyme can be targeted to cleave the unspliced p53 pre-mRNA through its catalytic activity without any effect on the integrity of the p53 mRNA. Since this ribozyme recognizes the GUC sequence and cleaves it most efficiently, it was determined whether a GUC sequence located at p53 codon 187 near the intron-exon boundary region in p53 pre-mRNA served as a site for ribozyme action. Efficient cleavage requires that one of the triplets GUC, GUU, GUA or UUC be present in the target RNA (Perriman et al., 1992; Ruffner et al., 1990). A GUA site is present at codon 262 near the intron 7—exon 8 boundary region. Two hammerhead ribozymes were designed for p53 pre-RNA and examined their in vitro cleavage activity and their biological activity in vivo.

An anti-p53 ribozyme (catalytic RNA) designed to cleave the p53 pre-messenger RNA efficiently reduces the level of endogenous mutant p53 mRNA. Retrovirus-mediated transduction of a hammerhead ribozyme (Rz5a) designed to cleave unspliced p53 RNA at codon 187 near the boundary of intron 5 and exon 6 reduced the level of mutant p53 RNA and protein in the human H226Br lung cancer cell line, which contains a homozygous p53 mutation at codon 254. The catalytic cleavage of the p53 pre-mRNA but not the p53 mRNA by the ribozyme was shown in vitro. The cleavage of the p53 pre-mRNA by this ribozyme was specific since a mutation in its catalytic domain (Rz5m) abolished the cleavage activity in vitro. Expression of the Rz5a ribozyme significantly suppressed the growth of the H226Br cells in culture. However, another ribozyme (Rz7a) targeted at codon 264 of the p53 gene near the boundary of intron 7 and exon 8 showed in vitro cleavage of the pre-mRNA but did not suppress cell growth. The site of modification in the p53 pre-mRNA may determine the degree of ribozyme-mediated growth suppression in this cell line. These findings that p53 pre-mRNA can be modified by a specific ribozyme in vivo indicate a role for these agents in gene therapy strategies for cancer.

A. Materials and Methods

1. Cell Lines

Human non-small cell lung cancer (NSCLC) cell line H226Br (obtained from Dr. I. J. Fidler) was cultured from a brain metastasis derived from the NIH-H226 cell line (obtained from Drs. J. D. Minna and A. F. Cazdar). H226Br has a homozygous point mutation (ATC to GTC) in codon 254 of the p53 gene. The H226Br cells were grown in RPMI medium, while the NIH-3T3 and ecotropic retrovirus packaging 02 (Mann et al., 1983) cell lines were grown in Dulbecco's modified Eagle's medium (DMEM) with glucose (4.5 g/l). The amphotropic packaging cell line GP+env Am12 (Markowitz et al., 1988b) was grown in DMEM containing glucose, 15 $\mu$g/ml hypoxanthine, 250 $\mu$g/ml xanthine, 25 $\mu$g/ml mycophrenolic acid and 200 $\mu$g/ml hygromycin (Sigma Chemical Co., St. Louis, Mo.). All these cell lines were supplemented with 10% fetal calf serum.

2. Ribozyme Synthesis and Creation of the Substrate RNA

Three ribozymes (Rz5a, Rz7a and Rz5m) and their p53 RNA substrates were produced for in vitro studies by using PCR with sequence-specific oligonucleotide primers. Rz5a was produced from two synthetic oligonucleotide primers, one containing a bacteriophage T7 polymerase promoter and complementary to the p53 exon 6 sequence, 5'-TAATACGACTCACTATAGGGCGAATTCGCTGAG GAGGGGCCACTGATCAGT-3' (SEQ ID NO:10), and the other corresponding to intron 5, 5'-GGATCCGATTGCTCTTAGGTTTCGTCCAAAAGG ACTCATCAGTGG-3' (SEQ ID NO:11). The primers were mixed. Because of a 12-bp overlapping sequence, they formed a hemiduplex structure which was amplified by PCR. A disabled, mutated form of this ribozyme (Rz5m) was produced by inserting a mutated base in one of the primers corresponding to the catalytic domain of the ribozyme. Rz5m was synthesized by using the primer containing the T7 promoter and a mutated primer, 5'-GGATCCGATTGCTCTTAGGTCTCGTCCAAAAGG ACTCATCAGTGG-3' (SEQ ID NO:12). A third ribozyme, Rz7a, which was targeted against intron 7—exon 8 of the p53 gene, was similarly produced from a primer containing the T7 promoter and complementary to exon 8, 5'-TAATACGACTCACTATAGGGCGAATTCTCCGTC CCAGTAGATCTGATG-3' (SEQ ID NO:13), and another corresponding to intron 7, 5'-TCCGGATCCTGAGTAGTGGTTTCGTCCAAAAGG ACTCATCAGATCTAC-3' (SEQ ID NO:14). A 84-bp PCR-amplified DNA sequence was identified in the gel. Purified PCR products were used for in vitro synthesis of the catalytic RNA using T7 RNA polymerase.

For in vivo analysis of ribozyme function, ribozymes were produced by PCR with flanking Stu I/Bg1 II restriction enzyme sites for cloning into an expression vector. All ribozymes contained the same core sequences mentioned above but no T7 promoter. Rz5a which was targeted against codon 187 (GUC), was PCR-amplified by using primers 5'-CCTGAGGAGGGGCCACTGATGAGTCCTTTTG-3' (SEQ ID NO:15) and 5'-TGATTGCTCTTAGGTTTCGTCCAAAAGGACTCA-3' (SEQ ID NO:16). The disabled ribozyme was produced (Rz5m) by using one mutated oligonucleotide primer 5'-TGATTGCTCTTAGGTCTCGTCCAAAAGGACTCA-3' (SEQ ID NO:17) and one of the primers mentioned above, which corresponds to p53 exon 6. Rz7a, which was targeted against codon 262 (GUA) of the p53 gene was also PCR-amplified by using the primers 5'-TCCTGAGTAGTGGTTTCGTCCAAAAGGACTCAT-3' (SEQ ID NO:18) and 5'-CCTTCCCAGTAGATCTGATGAGTCCTTTTGGAC-3' (SEQ ID NO:19). All three PCR products were subcloned into the Stu I/Bgl II site of the LNSX retroviral vector (Kashani-Sabet et al., 1992), in which expression of the ribozyme was driven by an SV40 promoter.

For production of ribozyme substrates, sequence-specific synthetic oligonucleotides corresponding to the 5' intron and 3' exon regions of the human p53 genomic DNA were synthesized (Applied Biosystems, Foster City, Calif., Model 392), and a 98 bp intron—exon junction sequence was amplified by using PCR. All the primers were selected so that each substrate-amplified PCR product was 98 bp long. A T7 bacteriophage promoter was attached to the 5' intron primer sequences so that T7 RNA polymerase could synthesize an 81-bp p53 pre-mRNA from the PCR DNA template in a cell-free system. Three areas of the p53 gene had been amplified by PCR to make substrate RNAs: 1) intron 5 and exon 6 junction sequence (pre-mRNA 5–6) using 5'-TAATACGACTCACTATAGGGCGAATTCCACTGAT TGCTCTTAGGTCTGGCCCCTCCT-3' (SEQ ID NO:20) corresponding to the intron 5 sequences and 5'-GGATCCACACGCAAATTTCCTTCCACTCGGATA AGATGCTGAGGAGGGGCCAGA-3' (SEQ ID NO:21) complementary to exon 6; 2) a portion of the p53 cDNA containing exon 5 and exon 6 sequences (mRNA 5–6) using the same exon 6 primer and the 5'-TAATACGACTCACTATAGGGCGAATTCTGCTCA GATAGCGATGGTCTGGCCCCTCCT-3' (SEQ ID NO:22) exon 5 primer with T7 promoter attached at the 5' end; and 3) an intron 7 and exon 8 junction sequence (pre-mRNA 7–8) using the 5'-TAATACGACTCACTATAGGGCGAATTCCCTATCC TGAGTAGTGGTAATCTACTGGGA-3' (SEQ ID NO:23) primer from the intron with T7 promoter at the 5' end and the 5'-CTCCGGATCCAGGCACAAACACGCACCTCAAA GCTGTTCCGTCCCAGTAGATTACCA-3' (SEQ ID NO:24) primer complementary to exon 8.

3. Synthesis of the Ribozymes and Substrate RNA by Transcription of the DNA Template The purified PCR-amplified DNA templates were used to synthesize the ribozymes and labeled substrate RNAs in vitro (Kashani-Sabet et al., 1992) at 37° C. using T7 RNA polymerase (0.5 μg DNA template; 40 mM Tris-HCl, pH 7.9; 20 mM MgCl$_2$; 10 mM NaCl; 10 mM dithiothreitol; 1 U RNasin; 0.5 mM each of ATP, CTP, and GTP; 0.05 mM UTP; 10 μCi [α $^{32}$P]UTP; and 20 U T7 RNA polymerase) for 30 min. The template DNA was removed by adding 2 U of RNase-free DNase (Promega Corp., Madison, Wis.), and the single-stranded RNA was purified by 12% polyacrylamide gel electrophoresis (PAGE) in the presence of 8 M urea.

An antisense p53 RNA probe was synthesized as above from a plasmid containing a p53 CDNA template. Amplimers corresponding to exon 5 [5'-TACTCCCCTGCCCTCAACAAG-3' (SEQ ID NO:25)] and exon 8 [5'-CTTAGTGCTCCCTGGGGGCAG-3' (SEQ ID NO:26)] were used to amplify a 500-bp p53 cDNA sequence by PCR from the complete p53 CDNA. This sequence was subcloned into the pGEM-3zf(−) transcription vector (Promega Corp). The RNA probe was used in northern blot hybridization.

4. In vitro Cleavage Reactions

In a 10 μl standard cleavage reaction, RNA substrates (0.2 μM) and ribozyme (0.3 μM) were mixed on ice. The reaction was initiated by adding a buffer containing 10 mM MgCl$_2$; 50 mM Tris HCl, pH 7.5; and 0.6 mM Na$_2$-EDTA. The reaction was carried out at 37° C. for 18 h and was stopped by adding an equal volume of stop buffer (95% formamide, 20 mM EDTA, 0.05% bromophenol blue, and 0.05% xylene cyanol), denatured at 80° C. for 2 min and subjected to PAGE on a 12% gel in the presence of 7 M urea. The gels were dried and autoradiographed. The cleavage products were quantified by phosphoimager (Molecular Dynamics, Sunnyvale, Calif.).

5. Production of a Ribozyme-producing Retrovirus

The PCR-amplified p53 ribozymes were subcloned into the LNSX retroviral vector, which contained a gene conferring neomycin resistance as a selectable marker. The transduction assay was done as described elsewhere (Cai et al., 1993). Briefly, the GP+env Am12 amphotropic packaging cell line was transfected with the LNSX-ribozyme constructs or with LNSX vector alone by using the calcium phosphate method, and clones resistant to G418 were selected. The virus-producing clones were mixed with ecotropic cell line ψ2 to increase the viral titer. The viral titers for Rz5a, Rz5m, and Rz7a were 5×10$^6$ colony-forming units (CFU/ml), 8×10$^6$ CFU/ml, and 4×10$^6$ CFU/ml, respectively. H226Br cells were seeded into 60-mm dishes, and cells were infected with ribozyme-producing viral supernatant at a multiplicity of infection of 10 in the presence of G418 (300 μg/ml). Each study was done in triplicate, and 14 days after infection, the G418-resistant colonies were counted. The resistant colonies were pooled and grown for another 2 weeks. Table 5 shows the results of colony formation in cell line H226Br.

TABLE 5

H226BR COLONY FORMATION AFTER INFECTION
NO. OF NEO-RESISTANT COLONIES OF H226BR CELLS

| Vectors | Exp. 1 | Exp. 2 | Exp. 3 | Mean ± SE |
|---|---|---|---|---|
| LNSX | 140 | 160 | 147 | 149 ± 10.1 |
| LNSRz5 (m) | 125 | 140 | 131 | 132 ± 7.5 |
| LNSRz7 (a) | 120 | 130 | 127 | 125 ± 5.1 |
| LNSRz5 (a) | 65 | 83 | 51 | 66 ± 16 |

6. Reverse Transcriptase PCR and Northern Blot Analysis

Total RNA extraction, reverse transcription, PCR amplification, and blot hybridization were performed as described elsewhere (Cai et al., 1993). In vivo expression of the ribozymes was detected by reverse transcriptase ("RT")-PCR using a primer sequence form the SV40 promoter of the LNSX vector [5'-CTATTCCAGAAGTAGTGAGGA-3' (SEQ ID NO:27)] and another from the catalytic domain of the ribozyme sequence [5'-TCGTCCAAAAGGACTCATCAG-3' (SEQ ID NO:28)]. The level of endogenous p53 expression was also assayed by RT-PCR using a primer corresponding to exon 1 [5'-GGGAGAAAACGTTAGGGTGTG-3' (SEQ ID NO:29)] and exon 4 [5'-TGCAAGTCACAGACTTGGCTG-3' (SEQ ID NO:9)] of p53. For northern blot analysis, the membrane was hybridized with an antisense p53 RNA probe as described above. Hybridization and washing were performed according to the protocols supplied by Promega Corporation.

B. Results

Figure 2:
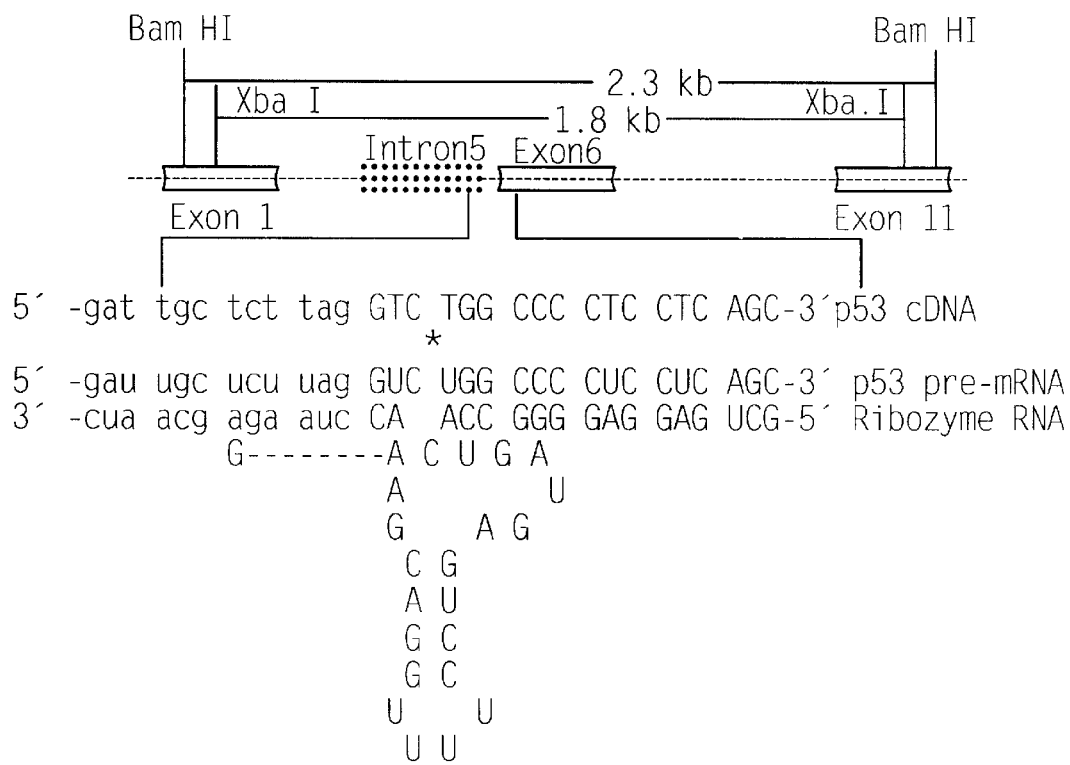
FIG. 2. The structure of the p53 ribozyme, shown with the conserved ribozyme sequence. The complementary p53 pre-mRNA is also shown with the GUC cleavage site. *, cleavage site; lower-case letters, partial intron 5 sequence; upper-case letters, partial exon 6 sequence; G - - - A, mutant ribozyme with G replacing A.

The hammerheaded ribozymes the inventors synthesized were designated Rz5a and Rz7a because of the positions of their cleavage sites:. Rz5a adjacent to the 3' end of intron 5 and Rz7 adjacent to the 3' end of intron 7 of the p53 gene. To confirm the specificity of the ribozyme action, a third disabled ribozyme was constructed which was identical to Rz5a except for one mutation, a base change in the catalytic domain of the ribozyme, and this was designated Rz5m. An example of the design of these ribozymes is shown in FIG. 2. The synthesis of the ribozymes was based on three parameters. First, the junction sequences between introns and exons of the p53 gene were selected as targets of ribozyme action. Second, a GUC site at codon 187 for Rz5a and a GUA site at codon 262 for Rz7a were selected for comparison of ribozyme cleavage activities and biological effects. Third, cleavage sites were located at the 5' end of the exon sequences close to the 3' adjacent intron sequences to specifically cleave the p53 pre-messenger RNA. Each ribozyme contained 22 bases of the highly conserved cleavage domain (McCall et al., 1992).

Figure 3:
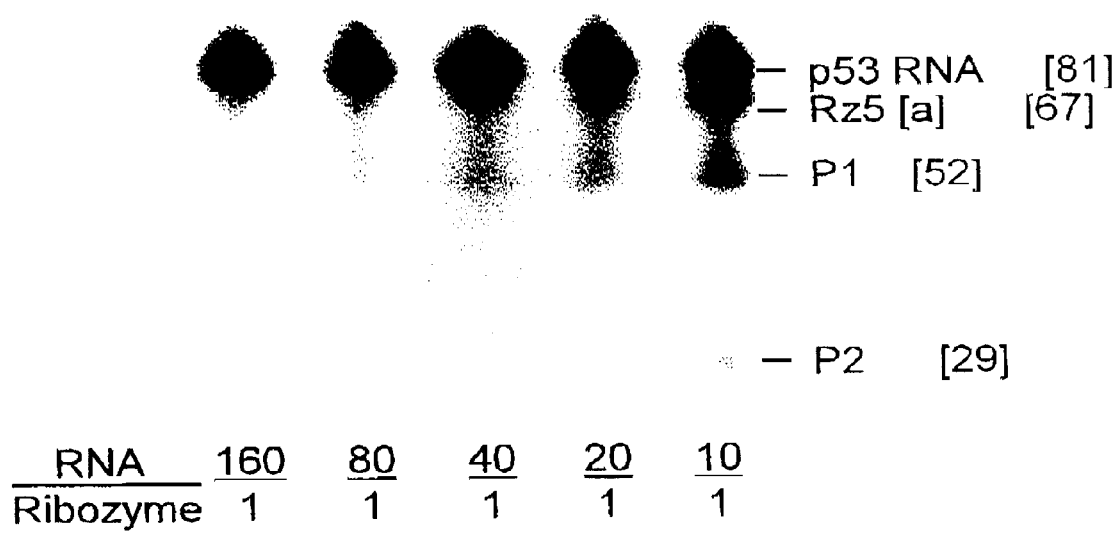
FIG. 3. Cleavage of the RNA substrate (intron 5 and exon 6) with decreasing RNA/ribozyme Rz5(a) molar ratios of the substrate RNA, 160:1 to 10:1.

Ribozymes in a cell-free system effected the in vitro cleavage of the p53 pre-RNA substrates. Ribozymes and their substrate RNA were synthesized separately by using T7 RNA polymerase, and gel purified. The labeled pre-mRNA substrates were efficiently cleaved by the Rz5a and Rz7a ribozymes in vitro. After the reaction, the products were separated in polyacrylamide gels, and two cleavage products, 29- and 52-bp fragments, were detected. The Rz5a ribozyme had no cleavage activity on p53 mRNA substrate, indicating the specificity of its action. Mutation of the functionally indispensable residue in the catalytic domain of the ribozyme disabled it so that it's cleavage activity was <3%. The results indicated that the efficiency of the ribozyme's cleavage activity depends on $Mg^{++}$ ion concentration. Cleavage reactions with decreasing ratios of the pre-mRNA 5–6 substrate to the Rz5a ribozyme are shown in FIG. 3.

Ribozymes were then subcloned into the LNSX retroviral vector (FIG. 1). The orientation of the ribozymes was determined by restriction enzyme digestion and further confirmed by PCR amplification using a 5' oligonucleotide primer derived from the SV40 promoter sequence and a 3' oligonucleotide primer corresponding to the catalytic domain of the ribozymes as described in the Material and Methods section. Human H226Br NSCLC cells, which have a mutation at codon 254 of p53 and express a mutant p53 protein, were then infected with these retroviral vectors. Following infection the cells were grown in the presence of G418 (300 µg/ml), and the number of resistant colonies was scored after 14 days. Introduction of the anti-p53 ribozyme Rz5a into the H226Br cell line substantially suppressed growth: the number of G418-resistant colonies was about twofold lower than in cells infected with vector only (control) or cells infected with the mutated Rz5m ribozyme in three separate studies (Table 5). However, the Rz7a ribozyme had no significant effect on colony formation.

Expression of the ribozymes was examined by isolating the total RNA from the stably infected clones by RT-PCR. Total RNA (2 µg per lane) was obtained from H226Br cells, H226Br-LNSRz5m cell, H226Br-LNSRz7a cells, and H226Br-LNSRz5a cells. Reverse transcriptase-PCR amplifications were performed followed by Southern blot analysis using catalytic domain of ribozyme or p53 cDNA as the probes. All three ribozymes, including the mutant form, were expressed at the same level in the transduced cell line. Although the RT-PCR assay was not quantitative, the expression of the active ribozyme was associated with a decrease in expression of the endogenous p53 mRNA.

Ribozymes Rz5a and Rz7a were both effective in reducing the level of p53 mRNA, whereas the mutant ribozyme had no effect on p53 expression in these cells. In northern blot analysis, neither a p53 RNA fragment cleaved by a ribozyme nor any low molecular weight RNA was detected in these transduced cells, presumably because the ribozyme-cleaved RNA was rapidly degraded by cellular RNase. Northern blot analysis was employed to illustrate p53 mRNA expression in p53 ribozyme-transduced H226Br cells (H226Br, H226Br-LNSRz5m, H226Br-LNSRz7a, and H226Br-LNSRz5a). In these instances the RNAs were hybridized with an antisense p53 (exons 5–8) RNA probe and the same blots were reprobed with a β-actin cDNA probe. The cells transduced with Rz5a expressed lower levels of the endogenous p53 mRNA than the control cells.

Figure 7:
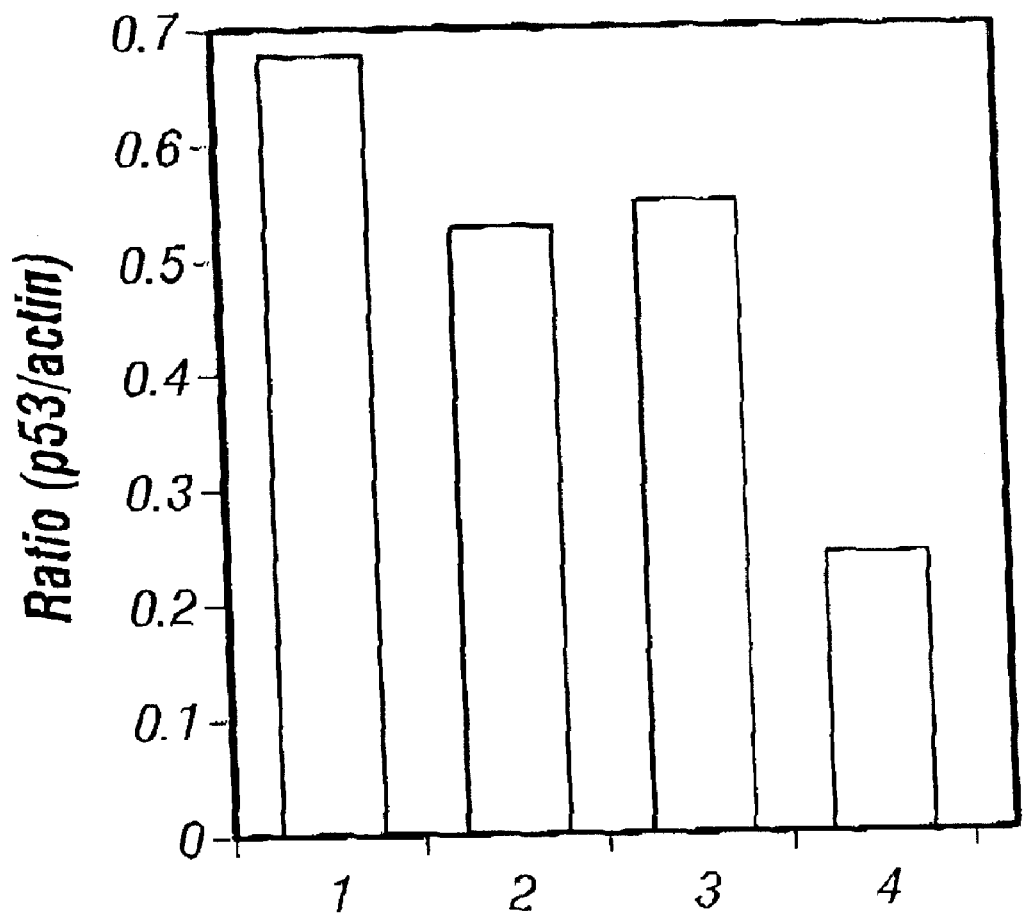

Western blot analysis of these ribozyme-transduced cells (H226Br, H226Br-LNSRz5m, H226Br-LNSRz7a, and H226Br-LSNRz5a) indicated that the ribozyme could efficiently reduce the level of the p53 protein. The p53 proteins were detected by a PAb1801 anti-p53 antibody. The same blots were reprobed with an anti-actin antibody. Densitometric analyses of the autoradiographs were done of the western blots. Each lane was scanned by using a Molecular Dynamics Computing Densitometer and the ratio (p53/actin) of full length p53 to actin was determined. For example, H226Br cells transduced with ribozyme Rz5a expressed 65% less mutated protein than parental control cells (FIG. 7). Cells transduced with ribozyme Rz7a expressed similar levels of mutated protein with a slightly lower control level.

Figure 4:
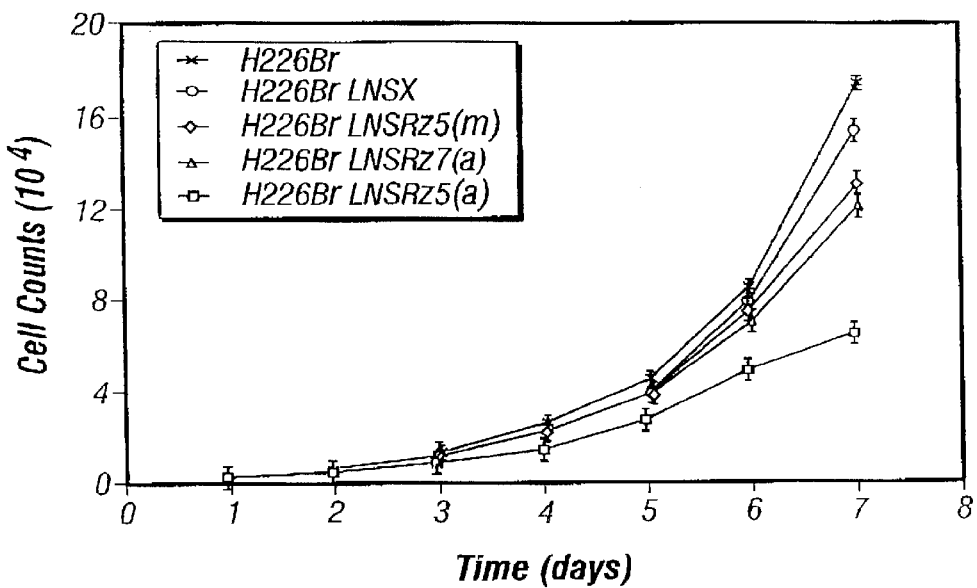
FIG. 4. Growth rates of transduced H226Br cells. Cells transduced and not transduced with the p53 ribozyme were plated in triplicate (2×10⁴ cells per well), and cells from three wells were counted each day for 7 days. The mean ±SE are shown. [H226Br●; H226Br-LNSX(O); H226Br-LNSRz5(m) (▼); H226Br-LNSRz7(a) (Δ); H226Br-LNSRz5(a) (■)].

To determine whether the observed change in the level of mutated p53 protein had biological significance, the effects of the ribozymes following transduction into H226Br cells was investigated (FIG. 4). The proliferation of H226Br cells transduced with the Rz5a ribozyme was inhibited by more than 50% (p<0.05) as compared to that of control untransfected cells or Rz5m-transduced cells. H226Br cells transduced with Rz7a ribozyme showed a marginal decrease in cell growth.

C. Discussion

Exploring alternative approaches to inactivating gene expression in tumors is important to the development of effective gene therapies for cancer. This example demonstrates that an active ribozyme is effective in reducing expression of the mutated p53 gene.

The ribozyme usually targets one of the following triplets: GUC, GUU, GUA or UUC. Studies in vitro showed that cleavage effects are similar for ribozymes targeting the triplet GUC (100%) and those targeting GUA (93%) (Perriman et al., 1992). The present example in vivo showed that a ribozyme targeting a GUC triplet is more effective than a ribozyme targeting a GUA triplet in reducing p53 mRNA and protein expression. These results were consistent with those of colony-formation and proliferation studies of transduced H226Br cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A pharmaceutical composition comprising:
   (i) an expression construct comprising a first promoter functional in eukaryotic cells and a first nucleic acid encoding a p53-specific ribozyme, wherein said first nucleic acid is under transcriptional control of said first promoter; and
   (ii) a pharmaceutically acceptable buffer, solvent or diluent.

2. The pharmaceutical composition of claim 1, wherein said expression construct further comprises a second nucleic acid encoding a functional p53, wherein the second nucleic acid transcript is not cleaved by said ribozyme.

3. The pharmaceutical composition of claim 2, wherein the expression construct further comprises a second promoter functional in eukaryotic cells, wherein said second nucleic acid is under the transcriptional control of said second promoter.

4. A method for treating a mammal with cancer comprising the steps of:
   (i) identifying a mammal having a cancer characterized by cells expressing a mutated, p53 product;
   (ii) providing an expression construct comprising (a) a first promoter functional in eukaryotic cells and a first nucleic acid encoding a p53-specific ribozyme, wherein said first nucleic acid is under transcriptional control of said first promoter and (b) a second nucleic acid encoding a functional p53 product, wherein the transcript from said second nucleic acid is not cleaved by said ribozyme; and
   (iii) contacting said expression construct with cancer cells in said mammal, whereby said ribozyme and said functional p53 products are expressed in said contacted cells, said ribozyme cleaving the transcript encoding said mutated p53 product.

5. The method of claim 4, wherein said second nucleic acid is a cDNA.

6. The method of claim 4, wherein said expression construct is a retrovirus.

7. The method of claim 4, wherein said ribozyme targets an intron-exon splice junction in a p53 transcript.

8. The method of claim 7, wherein said ribozyme targets p53 codon 187.

9. The method of claim 4, wherein said first promoter is selected from the group consisting of SV40 IE promoter, adenovirus major late promoter, CMV promoter, vaccinia virus 7.5K promoter or RSV LTR.

10. The method of claim 4, wherein said expression construct further comprises a polyadenylation signal.

11. The method of claim 4, wherein said expression construct is an adenovirus.

12. The method of claim 4, wherein said expression construct is an adeno-associated virus.

13. The method of claim 4, wherein said expression construct is a vaccinia virus.

14. The method of claim 4, wherein said expression construct is a herpesvirus.

15. The method of claim 4, wherein said contacting is effected by regional delivery of the expression construct.

16. The method of claim 4, wherein said contacting is effected by injection of a tumor with the expression construct.

17. The method of claim 4, further comprising the step, prior to said contacting, of tumor resection.

18. The method of claim 4, wherein said cancer is lung cancer.

19. The method of claim 4, wherein said cancer is breast cancer.

20. The composition of claim 2, wherein said first promoter is selected from the group consisting of SV40 IE promoter, adenovirus major late promoter, CMV promoter, vaccinia virus 7.5K promoter or RSV LTR.

21. The composition of claim 2, wherein said expression construct further comprises a polyadenylation signal.

22. The composition of claim 2, wherein said expression construct is an adenovirus.

23. The composition of claim 2, wherein said expression construct is an adeno-associated virus.

24. The composition of claim 2, wherein said expression construct is a vaccinia virus.

25. The composition of claim 2, wherein said expression construct is a herpesvirus.

* * * * *